United States Patent
Hayakawa et al.

(10) Patent No.: US 10,004,899 B2
(45) Date of Patent: Jun. 26, 2018

(54) ELECTRIC PULSE GENERATOR FOR ELECTROPORATOR AND ELECTROPORATOR APPARATUS PROVIDED WITH ELECTRIC PULSE GENERATOR

(71) Applicant: NEPA GENE CO., LTD., Ichikawa-shi (JP)

(72) Inventors: Yasuhiko Hayakawa, Ichikawa (JP); Kiyoshi Hayakawa, Ichikawa (JP); Masahiko Sugiyama, Hamamatsu (JP); Dai Ayusawa, Kawasaki (JP); Kensuke Miki, Kita-ku (JP)

(73) Assignee: NEPA GENE CO., LTD., Ichikawa-shi (JP)

( * ) Notice: Subject to any disclaimer, the term of this patent is extended or adjusted under 35 U.S.C. 154(b) by 21 days.

(21) Appl. No.: 15/370,918

(22) Filed: Dec. 6, 2016

(65) Prior Publication Data

US 2017/0080222 A1    Mar. 23, 2017

Related U.S. Application Data

(63) Continuation of application No. PCT/JP2014/084187, filed on Dec. 24, 2014.

(30) Foreign Application Priority Data

Jul. 28, 2014 (JP) ................. 2014-152730

(51) Int. Cl.
*A61N 1/32* (2006.01)
*A61N 1/30* (2006.01)
(Continued)

(52) U.S. Cl.
CPC .............. *A61N 1/327* (2013.01); *A61N 1/30* (2013.01); *C12N 15/09* (2013.01); *H03K 3/00* (2013.01); *C12M 35/02* (2013.01)

(58) Field of Classification Search
None
See application file for complete search history.

(56) References Cited

U.S. PATENT DOCUMENTS

| | | |
|---|---|---|
| 2002/0042588 A1 | 4/2002 | Jaroszeski et al. |
| 2004/0029240 A1 | 2/2004 | Acker |

(Continued)

FOREIGN PATENT DOCUMENTS

| | | |
|---|---|---|
| CN | 2160664 Y | 4/1994 |
| CN | 201261786 Y | 6/2009 |

(Continued)

OTHER PUBLICATIONS

Extended European Search Report dated May 22, 2017 in Patent Application No. 14898519.5.

(Continued)

*Primary Examiner* — Ankit D Tejani
(74) *Attorney, Agent, or Firm* — Oblon, McClelland, Maier & Neustadt, L.L.P.

(57) ABSTRACT

An electric pulse generator for electroporator includes a poring pulse generator, and a transfer pulse generator. The poring generator includes an n-stage Cockroft-Walton circuit, and a first circuit branched from a branching point of wiring on output side of the Cockroft-Walton, the first circuit includes a switching switch that is turned off in high-voltage mode and turned on in low-voltage mode, a voltage value for switching between the modes is in 200 to 1400 V, the first circuit includes a second circuit in which $m_2$ series of $m_1$ series-connected capacitors are connected in parallel, the switch and second circuit are connected in series, and first wiring on output side of the second circuit is merged with second wiring on output side of the Cockroft-Walton on (Continued)

output side of the branching point, and a withstand voltage of the Cockroft-Walton is a value in 1500 to 5000 V in the high-voltage mode.

20 Claims, 11 Drawing Sheets

(51) Int. Cl.
*C12N 15/09* (2006.01)
*H03K 3/00* (2006.01)
*C12M 1/42* (2006.01)

(56) References Cited

U.S. PATENT DOCUMENTS

| | | | |
|---|---|---|---|
| 2008/0103355 A1* | 5/2008 | Boyden | A61B 5/0071 600/103 |
| 2010/0021038 A1 | 1/2010 | Schulz | |
| 2012/0195080 A1* | 8/2012 | Smith | H02M 7/10 363/61 |
| 2012/0203297 A1 | 8/2012 | Efimov et al. | |
| 2013/0122592 A1 | 5/2013 | Hayakawa et al. | |
| 2013/0271166 A1* | 10/2013 | Bouffard | G01N 27/221 324/750.01 |
| 2014/0049997 A1* | 2/2014 | Freeman | H02M 7/539 363/97 |
| 2015/0151134 A1 | 6/2015 | Efimov et al. | |
| 2015/0287580 A1 | 10/2015 | Mizutani | |
| 2017/0080243 A1 | 3/2017 | Efimov et al. | |

FOREIGN PATENT DOCUMENTS

| | | |
|---|---|---|
| CN | 102441231 A | 5/2012 |
| CN | 103146750 A | 6/2013 |
| JP | 2002-532166 A | 10/2002 |
| JP | 2004-245811 A | 9/2004 |
| JP | 2006-314559 A | 11/2006 |
| JP | 2010-512535 A | 4/2010 |
| JP | 2013-085813 A | 5/2013 |
| JP | 2013-198637 A | 10/2013 |
| WO | WO 2000/035532 A1 | 6/2000 |
| WO | WO 03/095019 A2 | 11/2003 |
| WO | WO 2008/072166 A1 | 6/2008 |
| WO | WO 2011/047387 A2 | 4/2011 |
| WO | WO 2011/089953 A1 | 7/2011 |
| WO | WO 2014/068780 A1 | 5/2014 |

OTHER PUBLICATIONS

Combined Chinese Office Action and Search Report dated Jul. 26, 2017 in Patent Application No. 201480079212.1 (with English Translation of Category of Cited Documents).
International Search Report issued in Application No. PCT/JP2014/084187 dated Mar. 10, 2015 with English Translation.

* cited by examiner

ELECTRIC PULSE GENERATOR FOR ELECTROPORATOR AND ELECTROPORATOR APPARATUS PROVIDED WITH ELECTRIC PULSE GENERATOR

CROSS-REFERENCE TO RELATED APPLICATIONS

This application is a continuation of International Application No. PCT/JP2014/084187, filed on Dec. 24, 2014, which is based upon and claims the benefit of priority from the prior Japanese Patent Application No. 2014-152730 filed Jul. 28, 2014, the contents of each of which is hereby incorporated by reference in its entirety

BACKGROUND OF THE INVENTION

Field of the Invention

The present invention relates to an electric pulse generator for a multi-stage electroporator. The present invention also relates to an electroporator apparatus provided with the pulse generator, and a gene introduction method using the apparatus.

Description of Background Art

JP 2013-198637A describes a power source for an electroporator.

SUMMARY OF THE INVENTION

According to one aspect of the present invention, an electric pulse generator for an electroporator includes a poring pulse generator, and a transfer pulse generator. The poring pulse generator includes an n-stage Cockroft-Walton circuit, where n represents any integer of 2 or more, and a first circuit that is branched from a branching point of wiring on an output side of the n-stage Cockroft-Walton circuit, the first circuit includes a switching switch that is turned off in a high-voltage mode and turned on in a low-voltage mode, a voltage value for switching between the high-voltage mode and the low-voltage mode being in a range of 200 to 1400 V, the first circuit also includes a second circuit in which $m_2$ series of $m_1$ series-connected capacitors are connected in parallel, where $m_1$ represents any integer of 1 or more, and $m_2$ represents any integer of 2 or more, the switching switch and the second circuit are connected in series, and first wiring, which is disposed on an output side of the second circuit, is merged with second wiring, which is disposed on the output side of the n-stage Cockroft-Walton circuit, on the output side of the branching point, and a withstand voltage of the n-stage Cockroft-Walton circuit is a value in a range of 1500 to 5000 V in the high-voltage mode.

According to another aspect of the present invention, a poring pulse generator includes an n-stage Cockroft-Walton circuit, where n represents any integer of 2 or more, and a first circuit that is branched from a branching point of wiring on an output side of the n-stage Cockroft-Walton circuit. The first circuit includes a switching switch that is turned off in a high-voltage mode and turned on in a low-voltage mode, a voltage value for switching between the high-voltage mode and the low-voltage mode being in a range of 200 to 1400 V, the first circuit also includes a second circuit in which $m_2$ series of $m_1$ series-connected capacitors are connected in parallel, where $m_1$ represents any integer of 1 or more, and $m_2$ represents any integer of 2 or more, the switching switch and the second circuit are connected in series, and first wiring, which is disposed on an output side of the second circuit, is merged with second wiring, which is disposed on the output side of the n-stage Cockroft-Walton circuit, on the output side of the branching point, and a withstand voltage of the n-stage Cockroft-Walton circuit is a value in a range of 1500 to 5000 V in the high-voltage mode.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
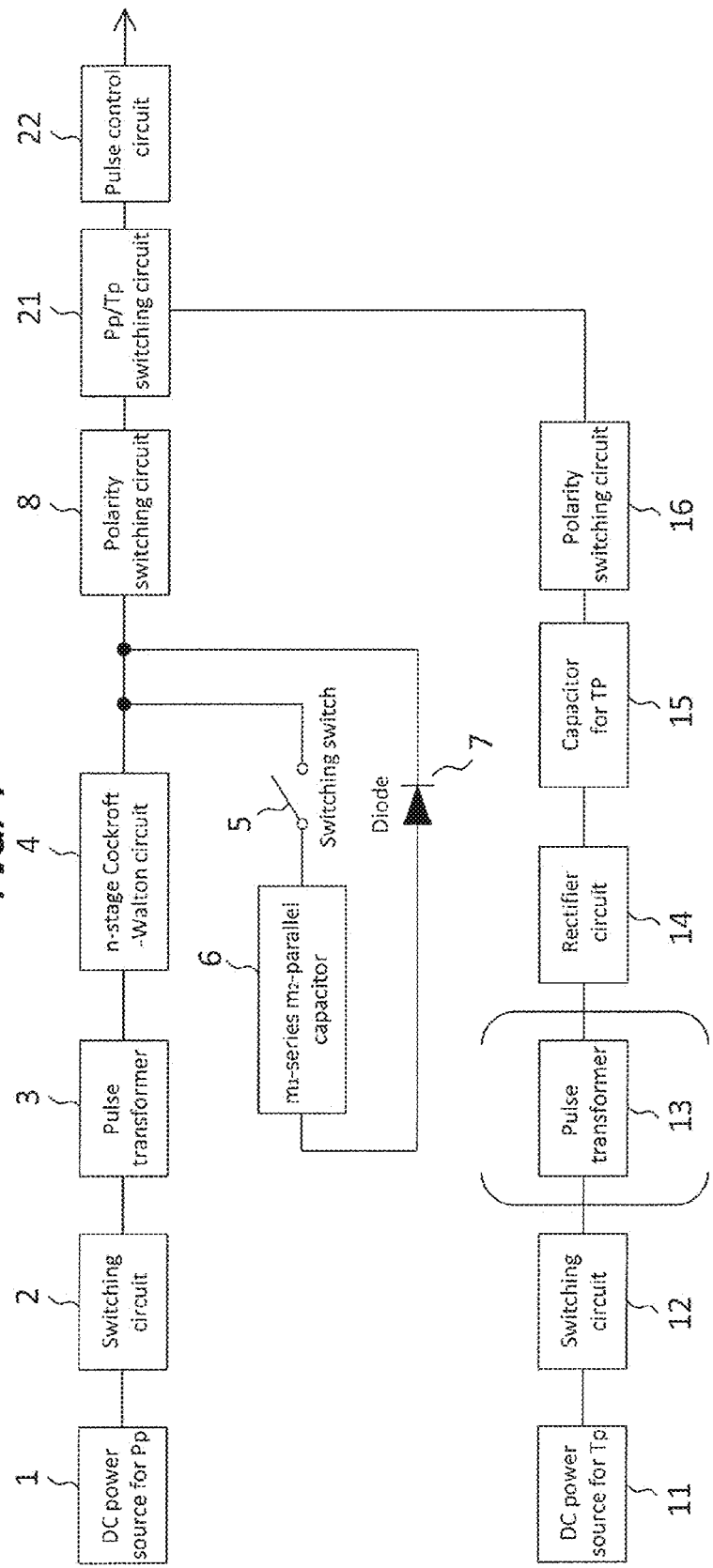
FIG. 1 is a configuration diagram showing a power source circuit according to an embodiment of the present invention.

The embodiments will now be described with reference to the accompanying drawings, wherein like reference numerals designate corresponding or identical elements throughout the various drawings.

Multi-Stage Electroporation Method

Multi-stage electroporation refers to electroporation method in multiple stages in which a high-voltage electric pulse having a short pulse width (referred to as "poring pulse" or "Pp" hereinafter) and a low-voltage electric pulse having a long pulse width (referred to as "transfer pulse" or "Tp" hereinafter) are applied successively.

In particular, it is known that multi-stage electroporation is an excellent technique with which the efficiency of introduction of genes into introduction targets can be dramatically improved when introducing genes into cells of mammals and the like.

However, in conventional technology, electroporator apparatuses that can be used for high-impedance subjects and have multiple stages have not been realized due to problems in manufacturing techniques handling a high-voltage power source circuit.

Moreover, in the electric pulse treatment of electroporation, solutions suitable for introduction targets and cytological properties (e.g., cell size and properties of the cell membrane) significantly vary depending on the species and types of cells, and therefore, electric pulse treatments under conditions suitable for respective introduction targets are needed.

Therefore, it has not been clear whether multi-stage electroporation is actually effective for species (e.g., bacteria and eukaryotic microorganisms) that are high-impedance subjects that require high-voltage pulse treatment. Moreover, nothing has been known about information regarding what kind of electric pulse conditions and the like are to be set when electroporation treatment is actually performed on species and cells that are high-impedance subjects.

Poring Pulse Generating Means

The pulse generator for an electroporator according to an embodiment of the present invention includes a poring pulse generating means.

This "poring pulse" refers to a high-voltage electric pulse that has a short pulse width and has a function of forming pores in the cell membranes of introduction targets in multi-stage electroporation.

The poring pulse may have a waveform of a square pulse or an exponential square pulse.

When low-impedance subjects are the introduction targets, it is sufficient that an output means for output on the order of several tens of volts to several hundreds of volts is used in order to obtain the necessary electric field intensity (V/cm). On the other hand, in the case of high-impedance subjects, there are cases where an output means for output on the order of several thousands of volts is needed.

The poring pulse generating means of the pulse generator according to an embodiment of the present invention is a power source circuit that includes a poring pulse generating direct-current power source, a capacitor charging circuit, and a capacitor circuit as substantial components. This power source circuit is not excluded from having a configuration including other circuit components and functional circuits as long as the functions of this power source circuit are not inhibited.

In this poring pulse generating means, with an aspect including one set of the direct-current power source and the capacitor charging circuit, multiple poring pulses in a broad range of several tens of volts to several thousands of volts can be generated successively, but aspects using separate power sources and charging circuits are not excluded.

Here, the poring pulse generating direct-current power source (DC power source 1) is a dedicated direct-current power source controlled to obtain a voltage peak value for generating a poring pulse. The capacitor charging circuit is connected to the output side of the direct-current power source 1.

Examples of the capacitor charging circuit include a circuit for transforming a direct current output by the direct-current power source 1 into a square wave (alternating current) and a circuit for boosting the square wave (alternating current).

For example, the capacitor charging circuit can be configured such that a switching circuit 2 is connected to the output side of the direct-current power source 1, and a pulse transformer 3 is connected to the output side of the switching circuit 2 in series. Here, the switching circuit 2 is a circuit for transforming direct current output by the direct-current power source 1 into a square wave (alternating current). The pulse transformer 3 is a circuit for boosting the square wave (alternating current).

With this circuit configuration, the voltage output by the capacitor charging circuit for a poring pulse is adjusted to have a value suitable as a voltage peak value before being input to an n-stage Cockroft-Walton circuit 4.

In this circuit configuration, the n-stage Cockroft-Walton circuit 4 serving as the capacitor circuit itself has a rectifying function, and therefore, it is not necessary to use a separate rectifier circuit after the pulse transformer 3 performs output. This is an advantage of employing the Cockroft-Walton circuit.

Cockroft-Walton Circuit

The output from the above capacitor charging circuit is input to the n-stage Cockroft-Walton circuit 4.

The n-stage Cockroft-Walton circuit 4 in this poring pulse generating power source circuit functions as a capacitor circuit in a high-voltage mode. In a low-voltage mode, the n-stage Cockroft-Walton circuit 4 functions as both a capacitor circuit and a capacitor charging circuit. (As will be described later, the poring pulse generating circuit according to an embodiment of the present invention is characterized in that the n-stage Cockroft-Walton circuit 4 also functions as a part of the capacitor charging circuit in the low-voltage mode.)

Figure 2:
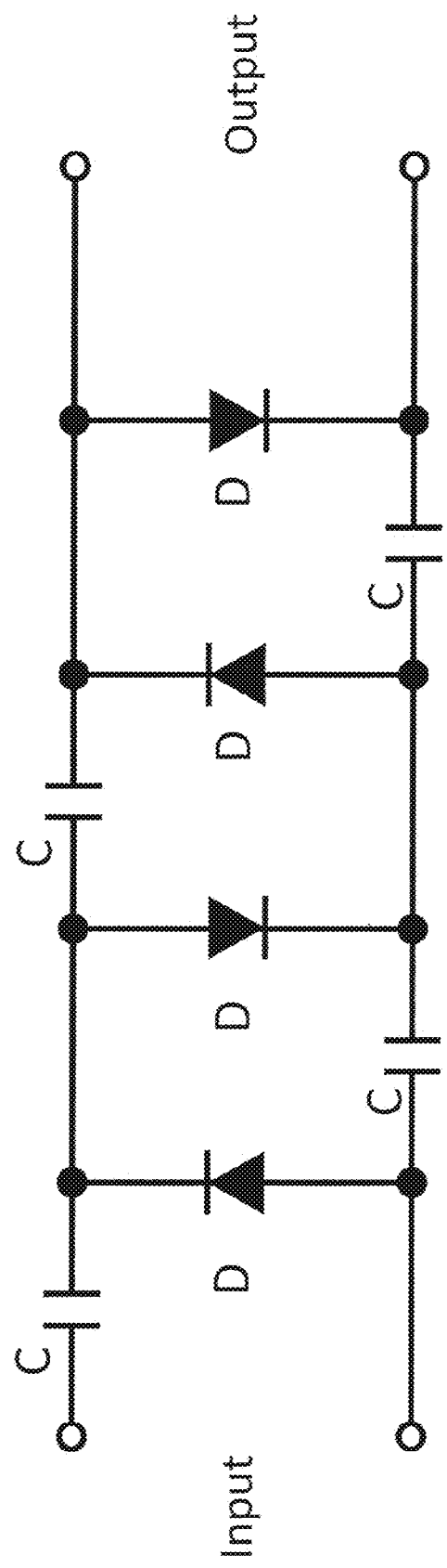
FIG. 2 is a diagram showing a circuit configuration of a two-stage Cockroft-Walton circuit (C indicates a capacitor, and D indicates a diode)
Figure 4:
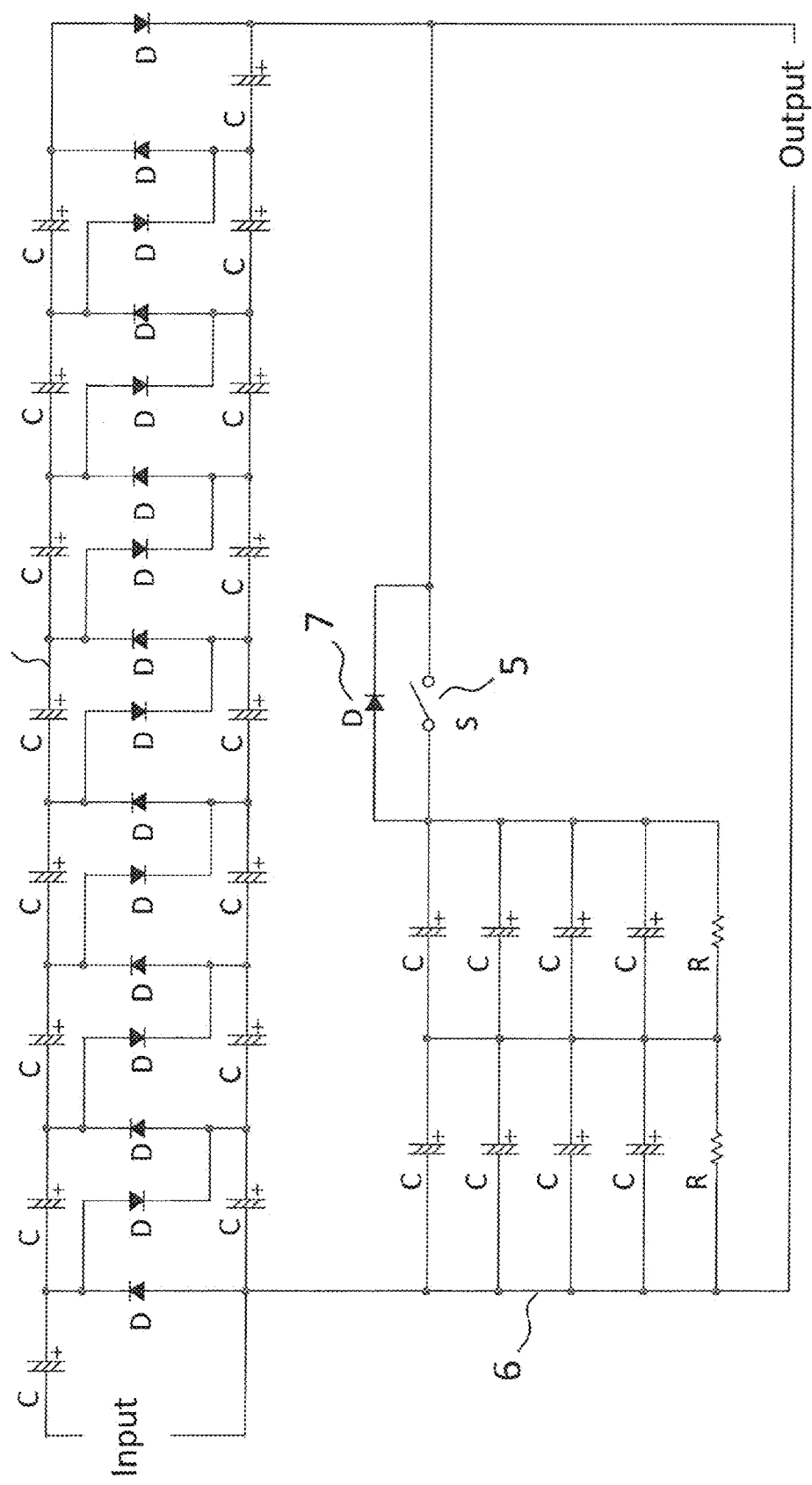
FIG. 4 is a circuit diagram showing an example of a capacitor circuit for a poring pulse according to an embodiment of the present invention (an example using an eight-stage Cockroft-Walton circuit and a two-series four-parallel capacitor circuit. C indicates a capacitor, D indicates a diode, S indicates a switching switch, and R indicates a resistor)

Here, the Cockroft-Walton circuit (also referred to as "CW circuit" hereinafter) is one type of a boost rectifier circuit configured by combining circuit component capacitors and diodes. An n-stage Cockroft-Walton circuit has a configuration of a circuit in which two series of n capacitors are connected in parallel via diodes. Here, n represents an integer of 2 or more. (FIG. 2 shows a two-stage Cockroft-Walton circuit, and FIG. 4 shows an eight-stage Cockroft-Walton circuit 4.)

There is no particular limitation on the capacitors used as the circuit components of this Cockroft-Walton circuit 4, but it is preferable to use commercially available chemical capacitors from the viewpoint of improving the productivity of apparatus manufacturing. It is particularly preferable to use capacitors having a withstand voltage of 500 V or lower, and preferably a withstand voltage of 450 V or lower.

On the other hand, the lower limit of the withstand voltage can be set to be greater than or equal to two times higher than the input voltage, for example, but it is preferable to use capacitors having a higher withstand voltage. It is preferable to use capacitors having a withstand voltage of 100 V or higher, preferably 200 V or higher, more preferably 300 V or higher, and even more preferably 360 V or higher, for example.

Specifically, commercially available capacitors having a withstand voltage of 300 V to 450 V, and preferably 360 to 450 V, are easily obtained and thus can be preferably used.

An advantage of use of the n-stage Cockroft-Walton circuit 4 is that such a high voltage generating circuit can be realized using commercially available capacitors having a low withstand voltage (and diodes).

Here, when an n-stage Cockroft-Walton circuit is built using component capacitors having the same withstand voltage and electric capacity, the withstand voltage of the circuit is n times higher than that of the component capacitors. The electric capacity of the n-stage Cockroft-Walton circuit is a factor of 2/n times that of the component capacitors.

It is preferable to use component capacitors having the same withstand voltage and electric capacity in the Cockroft-Walton circuit, but aspects using capacitors having different withstand voltages and electric capacities in combination are also included.

As long as the withstand voltage is in a range not deviating from the output voltage as a poring pulse and a sufficient electric capacity can be secured, any integer value can be employed as the number represented by n in the n-stage Cockroft-Walton circuit 4.

It is sufficient that the number represented by n is any integer of 2 or more, but any number of stages can be preferably employed as long as the value is in a range that preferably allows the later-mentioned withstand voltage and electric capacity to be secured.

Specifically, an example of the value represented by n is 4 or more, preferably 5 or more, more preferably 6 or more, even more preferably 7 or more, and even more preferably 8 or more.

An example of the upper limit thereof is 48 or less, preferably 36 or less, more preferably 24 or less, even more preferably 20 or less, even more preferably 16 or less, even more preferably 15 or less, even more preferably 14 or less, even more preferably 13 or less, even more preferably 12 or less, and even more preferably 11 or less.

An example of the value represented by n is 4 to 13, preferably 4 to 12, more preferably 5 to 11, even more preferably 6 to 10, and even more preferably 7 to 9.

It is preferable that the n-stage Cockroft-Walton circuit 4 has a withstand voltage of 1500 V or higher, preferably 1800 V or higher, more preferably 2000 V or higher, even more preferably 2200 V or higher, and even more preferably 2400 V or higher, for example.

Although it is sufficient that the upper limit thereof is in a range not deviating from the output voltage as a poring pulse in the high-voltage mode, an example thereof is 5000 V or lower, preferably 4600 V or lower, more preferably 4200 V or lower, even more preferably 4000 V or lower, even more preferably 3800 V or lower, even more preferably 3600 V or lower, even more preferably 3400 V or lower, and even more preferably 3200 V or lower.

When a voltage in the above-mentioned range of the withstand voltage is to be output as a poring pulse, the n-stage Cockroft-Walton circuit 4 needs to have an electric capacity of 20 μF or more, preferably 30 μF or more, more preferably 40 μF or more, even more preferably 50 μF or more, and even more preferably 55 μF or more, for example. The reason for this is that, though the voltage peak value of the output pulse is unlikely to attenuate in the case where the subject is a high-impedance subject, electric capacity higher than a certain level is required in order to successively generate a sufficient number of pulses.

The higher the upper limit of the electric capacity is, the better it is. An example of the upper limit is 500 μF or less, preferably 470 μF or less, more preferably 450 μF or less, even more preferably 400 μF or less, even more preferably 300 μF or less, even more preferably 220 μF or less, even more preferably 200 μF or less, even more preferably 150 μF or less, even more preferably 120 μF or less, even more preferably 100 μF or less, and even more preferably 80 μF or less.

The relationship between the withstand voltage value and the electric capacity in the case where Cockroft-Walton circuits are built using component capacitors shown in tables below is shown as an example.

The values shown in Tables 1 and 2 below are values that can be used as the basis descriptions of the upper limit and the lower limit of the value range. ("CW circuit" in the tables is an abbreviation for "Cockroft-Walton circuit".)

TABLE 1

| Number of stages of | Withstand voltage of CW circuit (V) | |
|---|---|---|
| n-stage CW circuit | Component capacitor has withstand voltage of 360 V | Component capacitor has withstand voltage of 450 V |
| 2 | 720 V | 900 V |
| 3 | 1080 V | 1350 V |
| 4 | 1440 V | 1800 V |
| 5 | 1800 V | 2250 V |
| 6 | 2160 V | 2700 V |
| 7 | 2520 V | 3150 V |
| 8 | 2880 V | 3600 V |
| 9 | 3240 V | 4050 V |
| 10 | 3600 V | 4500 V |
| 11 | 3960 V | 4950 V |
| 12 | 4320 V | 5400 V |
| 13 | 4680 V | 5850 V |
| 14 | 5040 V | 6300 V |

TABLE 2

| Number of stages of n-stage CW circuit | Electric capacity of CW circuit (μF) | |
|---|---|---|
| | Component capacitor has electric capacity of 220 μF | Component capacitor has electric capacity of 470 μF |
| 2 | 220.0 μF | 470.0 μF |
| 3 | 146.7 μF | 313.3 μF |
| 4 | 110.0 μF | 235.0 μF |
| 5 | 88.0 μF | 188.0 μF |
| 6 | 73.3 μF | 156.7 μF |
| 7 | 62.9 μF | 134.3 μF |
| 8 | 55.0 μF | 117.5 μF |
| 9 | 48.9 μF | 104.4 μF |
| 10 | 44.0 μF | 94.0 μF |
| 11 | 40.0 μF | 85.5 μF |
| 12 | 36.7 μF | 78.3 μF |
| 13 | 33.8 μF | 72.3 μF |
| 14 | 31.4 μF | 67.1 μF |

Branching-Merging Circuit

The poring pulse generating power source circuit is characterized by having a predetermined branching-merging circuit on the output side of the n-stage Cockroft-Walton circuit 4.

Specifically, the branching-merging circuit refers to a circuit that is branched from the branching point of the wiring on the output side of the n-stage Cockroft-Walton circuit 4, the branching-merging circuit including a predetermined switching switch 5 and an $m_1$-series $m_2$-parallel capacitor circuit 6 that are connected to each other in series, the wiring on the output side of the $m_1$-series $m_2$-parallel capacitor circuit 6 being again merged with the wiring on the output side of the n-stage Cockroft-Walton circuit 4 at a position on the output side with respect to the branching point.

This circuit is not excluded from having a circuit configuration including other circuit components and functional circuits as long as the functions of this circuit are not inhibited.

This branching-merging circuit is a characteristic part of the power source circuit according to an embodiment of the present invention. With a circuit configuration that merely uses the above-mentioned n-stage Cockroft-Walton circuit 4 and $m_1$-series $m_2$-parallel capacitor 6 in combination, a predetermined voltage cannot be obtained, and thus the charging of the capacitors cannot be achieved.

For example, the charging of the capacitors cannot be achieved merely by sending the output from the pulse transformer 3 directly to the $m_1$-series $m_2$-parallel capacitor 6 by bypassing the n-stage Cockroft-Walton circuit 4. In this case, a separate booster circuit is needed in order to obtain the voltage necessary to generate voltage in the low-voltage mode. Moreover, a direct-current power source for high voltage may be needed as necessary. Furthermore, a separate rectifier circuit for rectifying a square wave is needed.

High-Voltage Mode/Low-Voltage Mode Switching Switch

The switching switch 5 in this circuit is a switch having a function of switching the high-voltage mode for a poring pulse and the low-voltage mode for a poring pulse. Specifically, the switching switch 5 is a switching switch that is turned off in the high-voltage mode and turned on in the low-voltage mode in which the voltage is not more than (or less than) the switching voltage value.

A circuit configuration in which this switching switch 5 is connected to the input side of the $m_1$-series $m_2$-parallel capacitor circuit 6 is required. If this switching switch 5 is not arranged on the input side of the $m_1$-series $m_2$-parallel capacitor circuit 6, the functions of the power source circuit according to an embodiment of the present invention cannot be exhibited.

$m_1$-Series $m_2$-Parallel Capacitor Circuit

The "$m_1$-series $m_2$-parallel capacitor circuit 6" is a circuit that functions as the "capacitor circuit" in the low-voltage mode for a poring pulse. The $m_1$-series $m_2$-parallel capacitor circuit 6 refers to a circuit in which $m_1$ component capacitors are connected in series and $m_2$ series thereof are connected in parallel.

The voltage input to this circuit 6 is the direct current voltage output by the n-stage Cockroft-Walton circuit 4, the direct current voltage being obtained by rectifying the square wave (alternating current) from the pulse transformer 3.

There is no particular limitation on the capacitors used as the circuit components of this circuit 6, but it is preferable to use commercially available chemical capacitors from the viewpoint of improving the productivity of apparatus manufacturing. It is particularly preferable to use capacitors having a withstand voltage of 500 V or lower, and preferably a withstand voltage of 450 V or lower. On the other hand, with regard to the lower limit thereof, it is preferable to use capacitors having a higher withstand voltage. It is preferable to use chemical capacitors having a withstand voltage of 100 V or higher, preferably 200 V or higher, more preferably 300 V or higher, and even more preferably 360 V or higher.

Specifically, commercially available capacitors having a withstand voltage of 300 V to 450 V, and preferably 360 to 450 V, are easily obtained and thus can be preferably used.

It is preferable to use component capacitors having the same withstand voltage and electric capacity for the $m_1$-series $m_2$-parallel capacitor circuit 6, but aspects using capacitors having different withstand voltages and electric capacities in combination are also allowed.

As long as the withstand voltage is in a range not deviating from the output voltage as a poring pulse in the low-voltage mode and a sufficient electric capacity can be secured, any integer value can be employed as the number represented by $m_1$, which is the number of capacitors in each series, and the number represented by $m_2$, which is the number of parallel series, in the $m_1$-series $m_2$-parallel capacitor circuit 6.

Specifically, it is sufficient that the number represented by $m_1$, which indicates the number of capacitors in series, is any integer of 1 or more, preferably 2 or more, for example. It is more preferably 2 to 6, even more preferably 2 to 5, and even more preferably 2 to 4, for example. (A mode in which $m_1$ is 1 is conceivable in a case where the component capacitor has a sufficiently high withstand voltage, and in this case, merely a parallel capacitor circuit is obtained.)

Specifically, it is sufficient that the number represented by $m_2$, which indicates the number of parallel series, is any integer of 2 or more, and an example thereof is preferably 2 or more, more preferably 3 or more, and even more preferably 4 or more.

An example of the upper limit thereof is 20 or less, preferably 15 or less, more preferably 12 or less, even more preferably 10 or less, even more preferably 8 or less, even more preferably 7 or less, and even more preferably 6 or less.

An example of the number represented by $m_2$ is 2 to 20, preferably 2 to 15, more preferably 2 to 10, even more preferably 2 to 9, even more preferably 3 to 8, even more preferably 4 to 7, and even more preferably 4 to 6.

Here, it is preferable that the withstand voltage in the low-voltage mode is 200 V or higher, preferably 300 V or higher, more preferably 400 V or higher, even more preferably 500 V or higher, and even more preferably 600 V or higher, for example.

Although it is sufficient that the upper limit thereof is in a range not deviating from the output voltage as a poring pulse in the low-voltage mode, an example thereof is 1400 V or lower, preferably 1200 V or lower, more preferably 1000 V or lower, and even more preferably 900 V or lower.

Moreover, it is sufficient that the $m_1$-series $m_2$-parallel capacitor circuit 6 has an electric capacity sufficient to obtain a sufficient electric capacity (later-described total electric capacity of the n-stage Cockroft-Walton circuit 4 and the $m_1$-series $m_2$-parallel capacitor circuit 6) that enables the successive generation of multiple pulses when electric pulses are output to low-impedance subjects in the low-voltage mode.

An example of the electric capacity is 500 μF or more, preferably 600 μF or more, more preferably 700 μF or more, and even more preferably 800 μF or more.

The higher the upper limit of the electric capacity is, the better it is. An example of the upper limit is 4000 μF or less, preferably 3000 μF or less, more preferably 2500 μF or less, even more preferably 2000 μF or less, even more preferably 1500 μF or less, and even more preferably 1200 μF or less.

The $m_1$-series $m_2$-parallel capacitor circuit 6 is not excluded from having a circuit configuration including other circuit components and functional circuits as long as the functions of this circuit are not inhibited. For example, a circuit in which a resistor and the like are incorporated can be used.

Also, the $m_1$-series $m_2$-parallel capacitor circuit 6 can have a configuration in which diodes are incorporated in a predetermined arrangement according to the application so as to be transformed into a Cockroft-Walton circuit having few stages. Here, an example of the Cockroft-Walton circuit having few stages is a Cockroft-Walton circuit having 2 to 4 stages, and preferably about 2 to 3 stages.

Current Control Circuit Component

It is desirable that the branching-merging circuit includes a current control circuit component located on the output side of the $m_1$-series $m_2$-parallel capacitor circuit. Here, a specific example of the current control circuit component is a diode 7 that is connected in a direction in which current flows toward the output side.

The diode 7 refers to a semiconductor diode (e.g., PN junction diode or Schottky junction diode). Two or more diodes may be connected to each other in series and used in order to secure the withstand voltage of the diodes.

The voltages applied by the $m_1$-series $m_2$-parallel capacitor circuit 6 and the n-stage Cockroft-Walton circuit 4 can be output in a superposed manner by the functions of the diode 7 in the low-voltage mode.

Switching Between High-Voltage Mode and Low-Voltage Mode

The poring pulse generating power source circuit is provided with a high-voltage mode/low-voltage mode switching means. In this circuit, specifically, the above-mentioned switching switch 5 is the circuit element that achieves the switching between the high-voltage mode and the low-voltage mode.

The voltage value serving as an index of the switching between the high-voltage mode and the low-voltage mode can be set to be a predetermined voltage value depending on the specification of the apparatus.

For example, any voltage value in a range of 200 to 1400 V, preferably 300 to 1200 V, more preferably 400 to 1100 V, even more preferably 500 to 1000 V, even more preferably 600 to 900 V, and even more preferably 700 to 900 V, can be set as the voltage value for the switching between the high-voltage mode and the low-voltage mode.

In a case where the switching voltage value is set to 800 V, for example, when a voltage higher than this value (or higher than or equal to this value) is to be output, the mode is switched to the high-voltage mode. When a voltage lower than or equal to this value (or lower than this value) is to be output, output is performed in the low-voltage mode.

Output in High-Voltage Mode

In the high-voltage mode, the switching switch 5 is in the off state. In this case, the $m_1$-series $m_2$-parallel capacitor circuit 6 is not charged, and only the n-stage Cockroft-Walton circuit 4 is charged. Therefore, in the high-voltage mode, electric charge stored in the n-stage Cockroft-Walton circuit 4 is used to output an electric pulse.

The square wave (alternating current) input to the n-stage Cockroft-Walton circuit is boosted and rectified, and then direct current voltage that is 2n times the input peak value is output at the output end of the circuit 4.

For example, when a square wave (alternating current) of 50 to 200 V is input by the pulse transformer 3, a direct current voltage of 800 to 3200 V is output by an eight-stage Cockroft-Walton circuit 4.

The value of the above-mentioned withstand voltage of the n-stage Cockroft-Walton circuit 4 can be set as the upper limit voltage value that can be output in the high-voltage mode. In particular, any voltage value in a range of 1500 to 5000 V, preferably 1800 to 4600 V, more preferably 2000 to 4000 V, even more preferably 2200 to 3600 V, and even more preferably 2400 to 3200 V, can be set as the upper limit voltage value that can be output in the high-voltage mode.

On the other hand, the lower limit output value in the high-voltage mode is inevitably the voltage value of the above-mentioned index of the switching between the high-voltage mode and the low-voltage mode.

In the high-voltage mode, a pulse having a pulse width of 0.01 to 100 milliseconds, preferably 0.05 to 75 milliseconds, more preferably 0.1 to 50 milliseconds, even more preferably 0.1 to 25 milliseconds, even more preferably 0.1 to 20 milliseconds, and even more preferably 0.1 to 15 milliseconds, can be output.

Pulses that are output to the high-impedance subjects can be successively generated once to 30 times, preferably once to 20 times, more preferably once to 15 times, even more preferably once to 12 times, even more preferably once to 10 times, and even more preferably once to 9 times, depending on the above-mentioned capacitor capacities. It is also possible to generate no pulse (0 time).

Regardless of the fact that the pulse output in the high-voltage mode is a high-voltage pulse, a high-voltage electric pulse having a stable waveform is output because the set voltage and the actual applied voltage value are extremely close to each other.

Output in Low-Voltage Mode

In the low-voltage mode, the switching switch 5 is in the on state. In this case, the output from the n-stage Cockroft-Walton circuit 4 is input to the $m_1$-series $m_2$-parallel capacitor circuit 6 via the switching switch 5.

Here, due to the function of the diode 7, electric charge is stored in both of the capacitor circuits, namely the n-stage Cockroft-Walton circuit 4 and the $m_1$-series $m_2$-parallel capacitor circuit 6, to charge the capacitor circuits. That is, the n-stage Cockroft-Walton circuit 4 serves as a charging source for the $m_1$-series $m_2$-parallel capacitor circuit 6.

With this circuit configuration, in the low-voltage mode, the electric charge stored in both the n-stage Cockroft-Walton circuit 4 and the $m_1$-series $m_2$-parallel capacitor circuit 6 is used to output an electric pulse.

Here, it is sufficient that the total electric capacity stored in both the n-stage Cockroft-Walton circuit 4 and the $m_1$-series $m_2$-parallel capacitor circuit 6 is an electric capacity sufficient to successively generate multiple pulses when electric pulses are to be output to a low-impedance subject. The reason for this is that in the case where electric pulses are to be applied to a low-impedance subject, if a sufficient electric capacity cannot be secured, a sufficient number of electric pulses cannot be generated.

An example of the total electric capacity is 500 µF or more, preferably 600 µF or more, more preferably 700 µF or more, and even more preferably 800 µF or more.

The higher the upper limit of the electric capacity is, the better it is. An example of the upper limit is 4000 µF or less, preferably 3000 µF or less, more preferably 2500 µF or less, even more preferably 2000 µF or less, even more preferably 1500 µF or less, and even more preferably 1200 µF or less.

Specifically, an example thereof is 500 to 4000 µF, preferably 500 to 3000 µF, more preferably 600 to 2500 µF, even more preferably 600 to 2000 µF, even more preferably 700 to 1500 µF, and even more preferably 800 to 1200 µF.

The case where an eight-stage Cockroft-Walton circuit 4 and a two-series four-parallel capacitor 6 are built using component capacitors having an electric capacity of 470 µF can be taken as a specific example of the low-voltage mode. In this case, the eight-stage Cockroft-Walton circuit 4 has an electric capacity of 55 µF, the two-series four-parallel capacitor 6 has an electric capacity of 940 µF, and thus an electric capacity of 995 µF in total can be obtained as the capacitor capacity of the entire circuit.

Moreover, the value of the withstand voltage of the entire circuit is the value of the withstand voltage of the two-series four-parallel capacitor circuit. For example, with regard to the output voltage, when the two-series four-parallel capacitor circuit is built using component capacitors having a withstand voltage of 450 V, a poring pulse of up to 900 V can be output.

A voltage value lower than or equal to the value of the withstand voltage of the $m_1$-series $m_2$-parallel capacitor circuit 6 can be set as the upper limit voltage value that can be output in the low-voltage mode. In practice, the voltage value of the above-mentioned index of the switching between the high-voltage mode and the low-voltage mode is the upper limit.

Output can be performed as long as the lower limit exceeds 0 V, and output can be performed particularly when the lower limit is 1 V or higher. In particular, any voltage value in a range of 0 to 200 V (excluding 0 V), preferably 1 to 175 V, more preferably 10 to 150 V, even more preferably 20 to 125V, even more preferably 30 to 120V, even more preferably 40 to 110 V, and even more preferably 50 to 100 V, can be set as the lower limit voltage value that can be output in the low-voltage mode.

In the low-voltage mode, a pulse having a pulse width of 0.01 to 500 milliseconds, preferably 0.05 to 300 milliseconds, more preferably 0.1 to 200 milliseconds, even more preferably 0.1 to 100 milliseconds, even more preferably 0.1 to 75 milliseconds, and even more preferably 0.1 to 50 milliseconds, can be output.

Pulses that are output to a low-impedance subject can be successively generated once to 30 times, preferably once to 20 times, more preferably once to 15 times, even more preferably once to 12 times, even more preferably once to 10 times, and even more preferably once to 9 times, depending on the above-mentioned capacitor capacities. It is also possible to generate no pulse (0 time).

Transfer Pulse Generating Means

Also, the pulse generator for an electroporator according to an embodiment of the present invention includes a transfer pulse generating means.

This transfer pulse refers to a low-voltage electric pulse that has a long pulse width and is applied immediately after the above-mentioned poring pulse is applied in multi-stage electroporation.

The functions of this transfer pulse make it possible to introduce a target material (e.g., nucleic acid) into cells through pores that have been opened in the cell membranes by a poring pulse.

The value of the electric field intensity (V/cm) required for the transfer pulse is relatively low, and therefore, it is sufficient that an output means for output on the order of several tens of volts to several hundreds of volts is provided.

The transfer pulse may have a waveform of a square pulse or an exponential square pulse.

The transfer pulse generating means is a power source circuit that includes a transfer pulse generating direct-current power source, a capacitor charging circuit, and a capacitor circuit as substantial components.

This circuit is not excluded from having a configuration including other circuit components and functional circuits as long as the functions of this circuit are not inhibited.

Here, the transfer pulse generating direct-current power source (DC power source 11) is a dedicated direct-current power source controlled to obtain a voltage peak value for generating a transfer pulse.

The capacitor charging circuit is connected to the output side of the direct-current power source 11. Examples of the capacitor charging circuit include a circuit for transforming a direct current output by the direct-current power source 11 into a square wave (alternating current), a circuit for boosting the square wave (alternating current), and a circuit for rectifying the square wave (alternating current).

Here, in the case where a direct-current power source 11 that outputs a sufficiently high voltage is employed, the capacitor charging circuit can be configured to have a circuit configuration in which a switching circuit 12 is connected to the output side of the direct-current power source 11 and a rectifier circuit 14 is connected to the output side of the switching circuit 12 in series.

Here, the switching circuit 12 is a circuit for transforming a direct current output by the direct-current power source 11 into a square wave (alternating current). The rectifier circuit 14 is a circuit for rectifying the square wave (alternating current) into direct current.

A circuit having both a switching function and a rectifying function can also be used instead of the switching circuit 12 and the rectifier circuit 14.

On the other hand, in the case where a direct-current power source 11 that outputs a low voltage is employed, a means for boosting the square wave (alternating current) needs to be provided on the output side of the switching circuit 12.

An example of this boosting means is a means in which a pulse transformer 13 is connected between the switching circuit 12 and the rectifier circuit 14. The square wave output by the switching circuit 12 can be boosted by the functions of this pulse transformer 13.

Also, an example of this boosting means is a means in which a voltage doubler rectifier circuit (see FIG. 3) is employed as the rectifier circuit 14 separately from the pulse transformer 13.

Here, the voltage doubler rectifier circuit refers to a high voltage generating circuit having a function of doubling the input voltage and rectifying the input into direct current. That is, in aspects employing the voltage doubler rectifier circuit, a direct current voltage obtained by rectifying a square wave (alternating current) is output, and thus a direct current obtained by doubling the input voltage is output.

Figure 3:
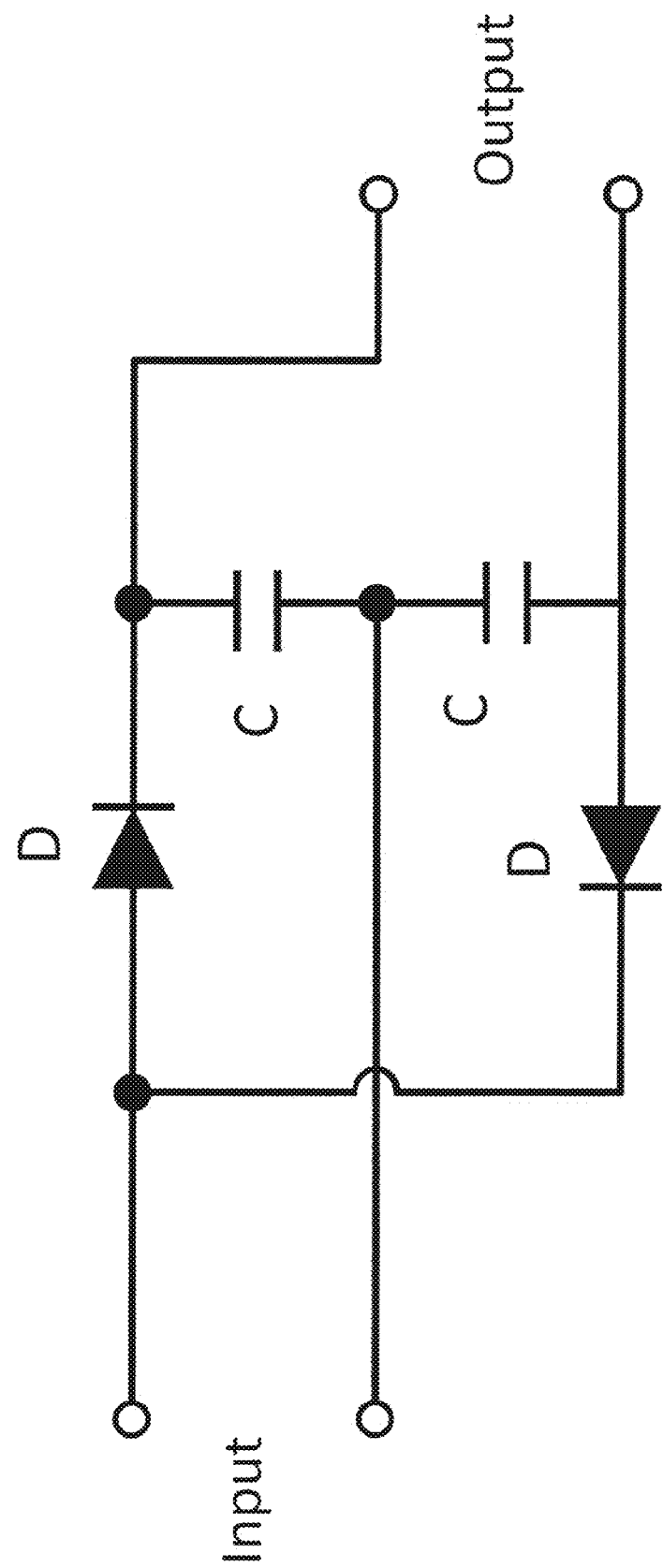
FIG. 3 is a diagram showing a circuit configuration of a voltage doubler rectifier circuit (C indicates a capacitor, and D indicates a diode)

It is sufficient that an electric pulse that requires a relatively low output voltage value is used as a transfer pulse in multi-stage electroporation, and therefore, the boosting means becomes unnecessary depending on the selected type of the direct-current power source 11. Moreover, even in the case where the boosting means is needed, the desired input voltage can be obtained by employing merely the pulse transformer 13 or the voltage doubler rectifier circuit (FIG. 3). The pulse transformer 13 and the voltage doubler rectifier circuit 14 can be used in combination.

The voltage generating means for a transfer pulse is not excluded from employing and/or being combined with a high voltage generating circuit (e.g., Cockroft-Walton circuit) other than the pulse transformer 13 and the voltage doubler rectifier circuit (FIG. 3).

With this circuit configuration, the voltage output by the "capacitor charging circuit" for a transfer pulse is adjusted to have a value suitable as a voltage peak value before being input to a capacitor 15 for a transfer pulse.

Capacitor Circuit for Transfer Pulse

It is preferable to use commercially available chemical capacitors having a withstand voltage of 500 V or lower, and preferably a withstand voltage of 450 V or lower, in the capacitor circuit 15 for a transfer pulse, from the viewpoint of improving the productivity of apparatus manufacturing. On the other hand, with regard to the lower limit, it is preferable to use capacitors having a higher withstand voltage. It is preferable to use capacitors having a withstand voltage of 100 V or higher, preferably 200 V or higher, more preferably 300 V or higher, and even more preferably 360 V or higher.

Specifically, commercially available capacitors having a withstand voltage of 300 V to 450 V, and preferably 360 to 450 V, are easily obtained and thus can be preferably used.

The desired function of the transfer pulse can be achieved by using merely an electric pulse that requires a relatively low output voltage value.

Therefore, it is sufficient that a circuit in which component capacitors are connected in parallel is used as the circuit 15, but a series capacitor circuit and/or a parallel capacitor circuit built by using component capacitors can be used depending on their withstand voltages and capacities. The desired function of the transfer pulse can be achieved by using merely an electric pulse that requires a relatively low output voltage value.

For example, capacitors having a withstand voltage of about 300 to 500 V, and preferably 360 to 450 V, can be used to obtain a desired withstand voltage by merely connecting the capacitors in parallel.

It is preferable to use component capacitors having the same withstand voltage and electric capacity in this circuit, but aspects using capacitors having different withstand voltages and electric capacities in combination are also allowed.

There is no particular limitation on the number of capacitors in parallel in this circuit 15 as long as a sufficient electric capacity is secured in the entire circuit 15. An example of the number of capacitors in parallel is any number in a range of 2 to 20, preferably from 4 to 16, more preferably from 6 to 14, and even more preferably from 7 to 15.

Here, it is preferable that the entire capacitor circuit 15 for a transfer pulse has a withstand voltage of 100 V or higher, preferably 150 V or higher, more preferably 200 V or higher, even more preferably 250 V or higher, and even more preferably 300 V or higher, for example.

Although it is sufficient that the upper limit thereof is in a range not deviating from the output voltage as a transfer pulse, an example thereof is 600 V or lower, preferably 500 V or lower, more preferably 450 V or lower, and even more preferably 400 V or lower.

Moreover, it is sufficient that the circuit 15 has an electric capacity that enables the successive generation of multiple pulses to be sufficiently secured even in a case where a low-impedance subject in which the voltage peak value attenuates significantly is assumed. An example of the electric capacity is 1000 μF or more, preferably 1200 μF or more, more preferably 1500 μF or more, and even more preferably 1800 μF or more.

The higher the upper limit of the electric capacity is, the better it is. An example of the upper limit is 5000 μF or less, preferably 4000 μF or less, more preferably 3500 μF or less, even more preferably 3000 μF or less, and even more preferably 2500 μF or less.

Output of Transfer Pulse

When a transfer pulse is generated, the electric charge stored in the above-mentioned capacitor circuit for a transfer pulse is used to output an electric pulse.

A transfer pulse can be output at a voltage that corresponds to the withstand voltage of the capacitor circuit for a transfer pulse. The output voltage can be 600 V or lower, preferably 500 V or lower, more preferably 400 V or lower, even more preferably 350 V or lower, and even more preferably 300 V or lower, for example. The output can be performed as long as the lower limit of the output voltage exceeds 0 V, and the output can be performed particularly when the lower limit of the output voltage is 1 V or higher.

A pulse having a pulse width of 0.01 to 1000 milliseconds, preferably 0.05 to 750 milliseconds, more preferably 0.1 to 500 milliseconds, even more preferably 0.1 to 250 milliseconds, even more preferably 0.1 to 200 milliseconds, even more preferably 0.1 to 150 milliseconds, and even more preferably 0.1 to 100 milliseconds, can be output as the transfer pulse.

Even in a case where a low-impedance subject in which the voltage peak value attenuates significantly is assumed, pulses can be successively generated once to 50 times, preferably once to 40 times, more preferably once to 30 times, even more preferably once to 25 times, and even more preferably once to 20 times, depending on the above-mentioned capacitor capacities. It is also possible to generate no pulse (0 time).

Control Means

It is desired that the pulse generator according to an embodiment of the present invention is provided with a control means for controlling the above-mentioned power source circuit in order to generate pulses that can be used in multi-stage electroporation.

Polarity Switching Circuit

It is preferable that the pulse generator includes a control means (polarity switching control means) that can switch the polarity of output voltage between positive polarity (+: plus) and negative polarity (−: minus). This means can be realized using polarity switching circuits 8 and 16.

In multi-stage electroporation, the electroporation efficiency can be further improved by applying a positive-polarity electric pulse followed by a negative-polarity electric pulse, which has been switched from the positive-polarity electric pulse. In particular, it is said that with an output waveform pattern obtained by applying the positive-polarity transfer pulse followed by the negative-polarity transfer pulse, exogenous materials can be introduced into cells with a further improved efficiency.

With regard to the position at which the polarity switching circuit is connected, an aspect is possible in which polarity switching circuits are respectively connected on the output side of the poring pulse generating power source circuit and on the output side of the transfer pulse generating power source circuit. In the case of this aspect, polarity reversal control is performed at the two positions.

In the case of this aspect, a polarity switching circuit 8 for a poring pulse is connected to the output side of the poring pulse generating power source circuit (to the output side of the merging point of the above-mentioned branching-merging circuit). On the other hand, a polarity switching circuit 16 for a transfer pulse is connected to the output side of the transfer pulse generating power source circuit (to the output side of the capacitor circuit for a transfer pulse).

Also, with regard to the position at which the polarity switching circuit is connected, an aspect is possible in which the polarity switching circuit is connected to the output side of a poring pulse/transfer pulse switching control circuit 21. In the case of this aspect, polarity reversal control is performed at only one position.

Poring Pulse/Transfer Pulse Switching Circuit

It is preferable that the pulse generator includes a means for merging the wiring from the poring pulse generating power source circuit and the wiring from the transfer pulse generating power source circuit, and switching and controlling the output. This means can be realized using a poring pulse/transfer pulse switching circuit 21.

It is sufficient that the position at which the poring pulse/transfer pulse switching circuit 21 is connected is located on the output side of the two power source circuits, namely the poring pulse generating power source circuit and the transfer pulse generating power source circuit.

Pulse Control Circuit

It is desired that in the pulse generator according to an embodiment of the present invention, the overall control of output pulses is achieved by using a pulse control circuit 22. It is preferable that this control circuit controls the pulse width, the pulse interval, and the number of output electric pulses, for example.

Also, in a case where a measurement unit for measuring the impedances of subjects, the actual applied voltage value, and the actual applied current value is provided, autonomous control can be performed such that the feedback of the information from these measurement values is performed to secure appropriate pulse generation (output value, waveform, and the like).

Electroporator Apparatus

The pulse generator according to an embodiment of the present invention can be used as a pulse generation source of an electroporator apparatus.

It is desired that the electroporator apparatus is provided with a power source control unit that controls input information and the like for the pulse generator. For example, it is desired that the power source control unit can control the pulse power source circuits in accordance with input information such as the switching between the high-voltage mode and the low-voltage mode, the voltage polarity switching, and the setting of various conditions for an electric pulse, during the operation of the apparatus.

A predetermined circuit configuration that enables a setting operation can be employed in the power source control unit.

Depending on the specification and the like of the apparatus, an apparatus that is equipped with a measurement device for measuring the impedances (resistances) of subjects, the actual applied voltage value, and the actual applied current value and has a function of displaying these values on a display unit can also be used. An apparatus that has a function of calculating the amount of generated electric pulse energy as a heat amount (J) using the measurement results and displaying it on a display unit such as a monitor can also be used. Moreover, an apparatus that can display the shape of the output pulse waveform on a display unit can also be used.

Here, with regard to a display means for displaying the output, the apparatus may have a built-in display unit such as a monitor, a liquid crystal display unit, or an LED display unit, or may be configured to include an external output terminal for performing output to an external display means. The apparatus can also be configured to display some information on a built-in display means and to output other information to the outside to display it. For example, an aspect connected to an oscilloscope or the like is also possible.

Furthermore, the apparatus can also be configured to have a terminal such as a USB or a Bluetooth function to output data to or store data in various PC-related devices such as a personal computer and a hard disk.

It is also preferable that the electroporator apparatus is configured to be provided with a safety device having a limiter function with respect to the generation of high voltage.

Regardless of the circuit configuration including only one set of the poring pulse generating direct-current power source and the capacitor charging circuit, the electroporation apparatus can be configured to perform the switching of the voltage of a poring pulse in an extremely broad range of several tens of volts to several thousands of volts depending on the difference in impedance among subjects. In addition, an extensive electric capacity in the low-voltage mode is achieved, and therefore, a sufficient number of pulses can also be generated with respect to low-impedance subjects.

Accordingly, with this electroporator apparatus, electroporation using a multi-stage electroporator can be applied to various target species and cells.

The power source circuit for a poring pulse according to this electroporator apparatus has a high-performance and simple circuit configuration and thus can be manufactured in an efficiently manufacturable manner in the manufacturing process. This configuration makes it possible to reduce the size by space saving.

Output Pulse

The pulse control circuit 22 successively outputs a poring pulse corresponding to the high-voltage mode or the low-voltage mode and a transfer pulse. A polarity-switched pulse can also be generated. The poring pulse and the transfer pulse can each be generated successively multiple times (see FIGS. 6 to 10).

Here, the waveform pattern of a pulse that can be output by using the electric pulse generator includes all waveforms that can be used in the multi-stage electroporation.

For example, two-stage output that successively outputs the poring pulse and the transfer pulse can be performed.

Also, three-stage output that successively outputs the poring pulse, the transfer pulse, and a polarity-switched transfer pulse can be performed.

Furthermore, four-stage output that successively outputs the poring pulse, the polarity-switched poring pulse, the transfer pulse, and a polarity-switched transfer pulse can be performed.

It is also possible to perform polarity switching frequently, thereby outputting the poring pulse, the polarity-switched poring pulse, the transfer pulse, and the polarity-switched transfer pulse in a desired rearranged order.

Of course, the poring pulse and the transfer pulse each can be generated successively multiple times.

Although the output pulse can be output in a square shape, the output pulse may have an exponential square pulse shape obtained by the pulse peak value drawing an attenuation curve depending on the types of connected electrodes and subjects. When multiple pulses are generated, a peak value generated at a second time or after may be as high as the peak value of the attenuated preceding pulse (in a case where the polarity has been switched, a peak value having an opposite polarity with the same absolute value may be obtained).

This attenuation is due to a phenomenon (natural attenuation) caused by applying the electric charge stored in the capacitor to the materials. Although the degree of this attenuation varies depending on the impedances of the connected electrode and the subjects, the degree of the attenuation becomes mild in a case of the high-impedance subjects.

In an embodiment of the present invention, a pulse in which a square shape is maintained can also be obtained by incorporating a means for controlling the pulse peak value as a pulse control means. Moreover, all the pulses can be output so as to have the same peak value.

Furthermore, in an embodiment of the present invention, the degree of attenuation of the pulse peak value can be controlled to form a pulse waveform that draws a desired attenuation curve.

There is no particular limitation on the interval between the generated pulses (pulse interval: e.g., the interval between the Pps, the interval between the Tps, and the interval between the Pp and the Tp), and an example thereof is 0.05 milliseconds to 100 seconds, preferably 0.5 milliseconds to 50 seconds, more preferably 5 milliseconds to 10 seconds, even more preferably 10 milliseconds to 5 seconds, even more preferably 25 milliseconds to 2.5 seconds, and even more preferably 50 milliseconds to 1 second.

Electroporation

This electroporator apparatus can be used in a multi-stage electroporation method suitable for various species and cells by connecting an electrode that has a desired shape and is made of a desired material corresponding to the application to wiring on the output side of the pulse control circuit 22. The obtained output pulse is successively applied to the subjects by a series of sequence control.

All currently available electrodes for electroporation can be used as a connectable electrode, and any of electrodes such as a cuvette electrode, a plate electrode, an electrode with legs, a needle electrode, a tweezers electrode, a rod electrode, and a petri dish electrode can be used.

Therefore, this electroporator apparatus can be used for electroporation in any situation such as in vitro, in vivo, ex vivo, or in ovo.

Figure 11:
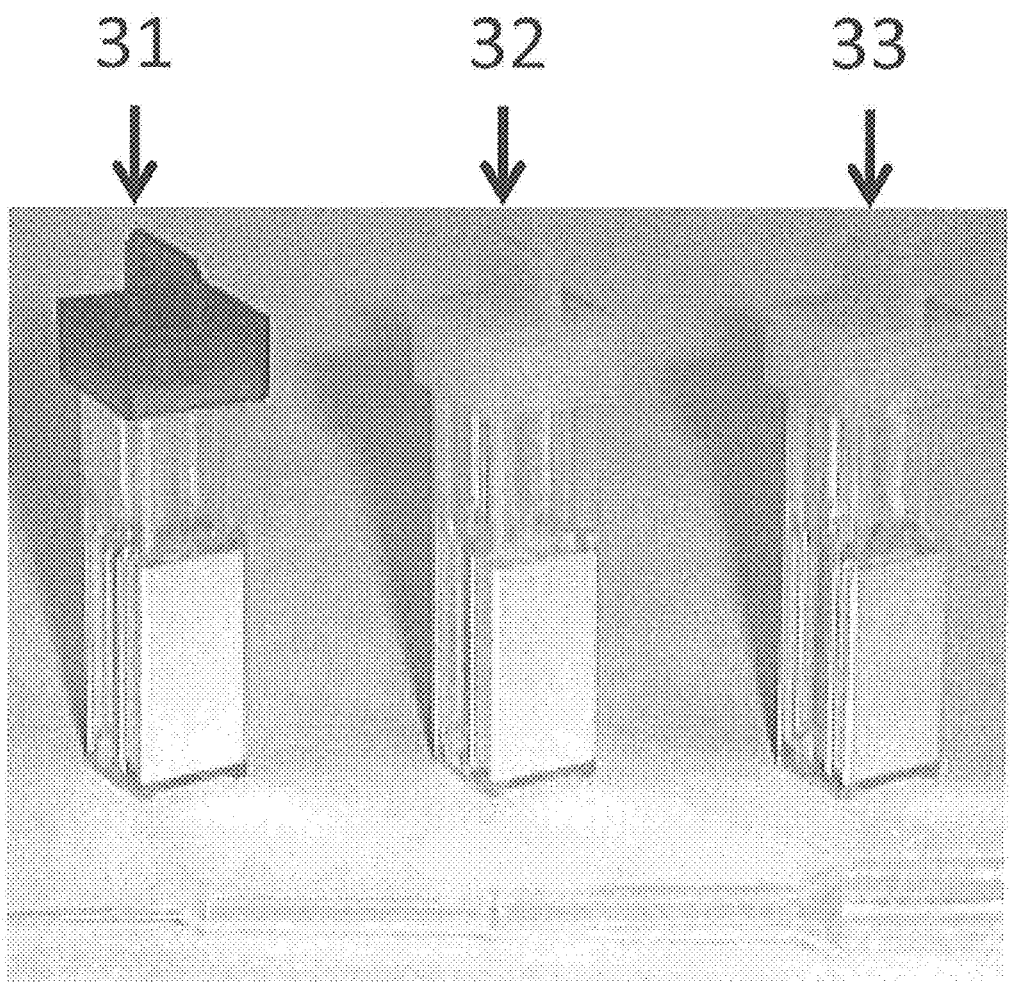
FIG. 11 is a photograph of external appearances of cuvette electrodes (31 indicates a cuvette electrode with a 1-mm gap, 32 indicates a cuvette electrode with a 2-mm gap, and 33 indicates a cuvette electrode with a 4-mm gap).

In particular, this electroporator apparatus is an apparatus that can achieve multi-stage electroporation for high-impedance subjects (e.g., bacteria and eukaryotic microorganisms), which has not been achievable by a conventional technique, and thus is expected to exhibit a particularly significant effect in an aspect using a cuvette electrode (see FIG. 11).

The high-impedance subjects used as electroporation samples refer to species and cells on which electroporation is performed using an aqueous solution containing glycerol, sugars, and the like (solution having high electric resistance) as a solution to be used in the electroporation from the viewpoint of suppressing cell injury and maintaining cell competency (transformation efficiency).

Examples thereof include sample solutions containing bacteria (specifically prokaryotes such as eubacteria, archaebacteria, and cyanobacteria), eukaryotic microorganisms (particularly unicellular eukaryotic organisms such as yeasts and protozoans, filamentous fungi such as mold, and the like), and the like.

In particular, this multi-stage electroporator can be used to achieve the introduction of genes, with an extremely high efficiency, into samples with which it is difficult to obtain a favorable gene introduction efficiency even using a high-voltage electroporation method using a conventional apparatus due to causes resulting from their cytological characteristics or microbiological characteristics.

It can be said that a solution having a high impedance in a range of 0.5 kΩ or higher, preferably 0.8 kΩ or higher, more preferably 1 kΩ or higher, even more preferably 2 kΩ or higher, even more preferably 3 kΩ or higher, even more preferably 4 kΩ or higher, and even more preferably 5 kΩ or higher, for example, is a solution having a high electric resistance.

There is no particular limitation on the upper limit as long as the upper limit is in a range in which a sufficient electric field intensity can be generated at the voltage of this electric pulse, and an example of the upper limit is 50 kΩ or lower, preferably 40 kΩ or lower, more preferably 30 kΩ or lower, and even more preferably 25 kΩ or lower.

Poring pulse sufficient for high-impedance subjects has an electric field intensity of 5 to 30 kV/cm, preferably 8 to 27 kV/cm, more preferably 9 to 25 kV/cm, even more preferably 10 to 24 kV/cm, even more preferably 11 to 23 kV/cm, even more preferably 12 to 22 kV/cm, even more preferably 13 to 21 kV/cm, and even more preferably 14 to 20 kV/cm, for example.

Moreover, the transfer pulse for high-impedance subjects has an electric field intensity of 0.01 to 4 kV/cm, preferably 0.05 to 3.5 kV/cm, more preferably 0.1 to 3 kV/cm, even more preferably 0.2 to 2.5 kV/cm, even more preferably 0.2 to 2 kV/cm, and even more preferably 0.5 to 2 kV/cm, for example.

This electroporator apparatus can perform multi-stage electroporation in the low-voltage mode by outputting an electric pulse to the tissues and cells (e.g., animal cells and plant cells) of species that are the low-impedance subjects.

Here, an example of the low-impedance range is less than 500Ω, preferably 450Ω or lower, more preferably 400 9 or lower, even more preferably 300Ω or lower, even more preferably 200Ω or lower, and even more preferably 100Ω or lower.

In this case, multi-stage electroporation can be performed with reference to conventional conditions for an electric pulse.

Particular examples of materials to be introduced into cells using this electroporator apparatus include nucleic acid molecules such as exogenous DNA and exogenous RNA, and other compounds and the like such as nucleic acid analogues, proteins, drugs, and fluorescent materials can also be introduced into cells efficiently.

In particular, this electroporator apparatus can be used preferably for transformation, transduction, functional deficiency, homologous recombination, and genome editing, using an exogenous gene introduction method. Specifically, this electroporator apparatus can also be used to introduce a plasmid DNA, a construct DNA, a virus vector, an antisense nucleic acid, an siRNA, and an oligonucleotide. Moreover, this electroporator apparatus can also be preferably used to introduce a nucleic acid analogue (e.g., morpholino polymer).

EXAMPLES

Hereinafter, an embodiment of the present invention will be described in detail by way of examples, but the present invention is not limited to the following examples.

Manufacturing Example 1

Electroporator Apparatus According to an Embodiment of the Present Invention

An electroporator apparatus provided with a pulse generator including the power source circuit shown in FIG. 1 was manufactured as the electroporator including the pulse generator according to an embodiment of the present invention.

(1) Poring Pulse Generating Power Source Circuit

A power source circuit for a poring pulse of this manufacturing example will be described. In this circuit, direct current from the DC power source 1 controlled for a poring pulse is transformed into a square wave by the switching circuit 2, boosted by the pulse transformer 3, and input to the eight-stage Cockroft-Walton circuit 4.

The two-series four-parallel capacitor 6 is connected to the output side of this eight-stage Cockroft-Walton circuit 4 via the switching switch 5, and a circuit including this two-series four-parallel capacitor 6 serves as a branching-merging circuit with respect to the wiring from the eight-stage Cockroft-Walton circuit 4.

The circuit has a circuit configuration in which the wiring from the eight-stage Cockroft-Walton circuit 4 and the wiring from the two-series four-parallel capacitor 6 are connected to each other at the merging point, and the polarity switching circuit 8 is connected to the output side of the merging point.

(i) High-Voltage Mode

In this embodiment, when the voltage is higher than 800 V, the mode is switched to the high-voltage mode, and the switching switch 5 is in the off state. In this case, only the eight-stage Cockroft-Walton circuit 4 is charged (the two-series four-parallel capacitor 6 is not charged).

This eight-stage Cockroft-Walton circuit 4 has a configuration in which two series of eight direct-connected capacitors are connected in parallel, and is charged by electric charge being stored in these built-in capacitors.

The voltage input to the eight-stage Cockroft-Walton circuit 4 is boosted and rectified by the functions of this circuit, and direct current voltage that is 2×8 times higher than the peak value of the input square wave is output at the output end of the circuit.

Each of the capacitors used in the eight-stage Cockroft-Walton circuit in this embodiment has a withstand voltage (Vc) of 450 V, and therefore, the eight-stage Cockroft-Walton circuit 4 has a withstand voltage of 3600 V (450 V×8).

Each of the capacitors used in the circuit 4 has a capacitor capacity (Cc) of 220 μF, and therefore, the capacitor capacity stored in the eight-stage Cockroft-Walton circuit 4 is 55 μF (220 μF/8×2).

Accordingly, in this embodiment, the eight-stage Cockroft-Walton circuit 4 serves as a capacitor circuit having a withstand voltage of 3600 V and a capacitor capacity of 55 μF.

As a result, in this high-voltage mode, the electric charge stored in the eight-stage Cockroft-Walton circuit 4 having an electric capacity of 55 μF is used as a pulse as a poring pulse.

This circuit 4 has a withstand voltage of 3600 V and thus can sufficiently withstand the generation of a poring pulse of 3000 V.

Moreover, considering the capacitor capacity, pulses can be successively generated once to nine times. It is also possible to generate no pulse (0 time).

(ii) Low-Voltage Mode

When the voltage output by the eight-stage Cockroft-Walton circuit 4 is lower than or equal to the upper limit of the voltage value in the low-voltage mode (here, 800 V or lower), the switching switch 5 is in the on state.

In this case, the output from the eight-stage Cockroft-Walton circuit 4 is applied to the two-series four-parallel capacitor 6 via the switching switch 5, and thus the two-series four-parallel capacitor 6 is charged.

That is, in the low-voltage mode, electric charge is stored in both the capacitor circuits, namely the eight-stage Cockroft-Walton circuit 4 and the two-series four-parallel capacitor 6, and thus charging is performed.

The output from the eight-stage Cockroft-Walton circuit 4 and the output from the two-series four-parallel capacitor 6 are superposed by the functions of the diode 7, and thus the charge in the capacitors of both the circuits is used as the electric charge for a poring pulse.

Each of the capacitors used in this two-series four-parallel capacitor circuit 6 has a withstand voltage (Vp) of 450 V, and therefore, the circuit 6 has a withstand voltage of 900 V (450 V×2).

Each of the capacitors used in this circuit has a capacitor capacity (Cp) of 470 μF, and therefore, the capacitor capacity stored in the circuit 6 is 940 μF (470 μF/2×4).

As a result, in this low-voltage mode, the capacitor capacity of the entire circuit is 995 μF that is the sum of 55 μF, which is the capacity of the eight-stage Cockroft-Walton circuit 4, and 940 μF, which is the capacity of the two-series four-parallel capacitor circuit 6. The entire circuit has a withstand voltage of 900 V and thus can sufficiently withstand the voltage of 800 V.

Moreover, considering the capacitor capacity, pulses can be successively generated once to nine times. It is also possible to generate no pulse (0 time).

(2) Transfer Pulse Generating Power Source Circuit

Next, a power source circuit for a transfer pulse of this manufacturing example will be described. In a means for generating a transfer pulse, a DC power source 11 controlled for a transfer pulse that is a power source separate from the DC power source 1 controlled for a poring pulse is used.

The circuit has a circuit configuration in which direct current from the DC power source 11 for a transfer pulse is transformed into a square wave by the switching circuit 12, rectified by the rectifier circuit 14, and input to the capacitor 15 for a transfer pulse. The electric charge stored in this capacitor 15 is used as an electric pulse for a transfer pulse.

The polarity switching circuit 16 is connected to the output side of the capacitor circuit 15 for a transfer pulse.

The transfer pulse in this embodiment is an electric pulse having a relatively low output voltage. A power source that can output the voltage of 300 V is used as the DC power source 11 for a transfer pulse, and therefore, a desired input voltage can be obtained without using a voltage boosting means.

In this embodiment, capacitors (each having a withstand voltage of 400 V and an electric capacity of 270 μF) used in the capacitor circuit 15 for a transfer pulse are connected not in series but in parallel in order to increase the capacitor capacity.

Figure 5:
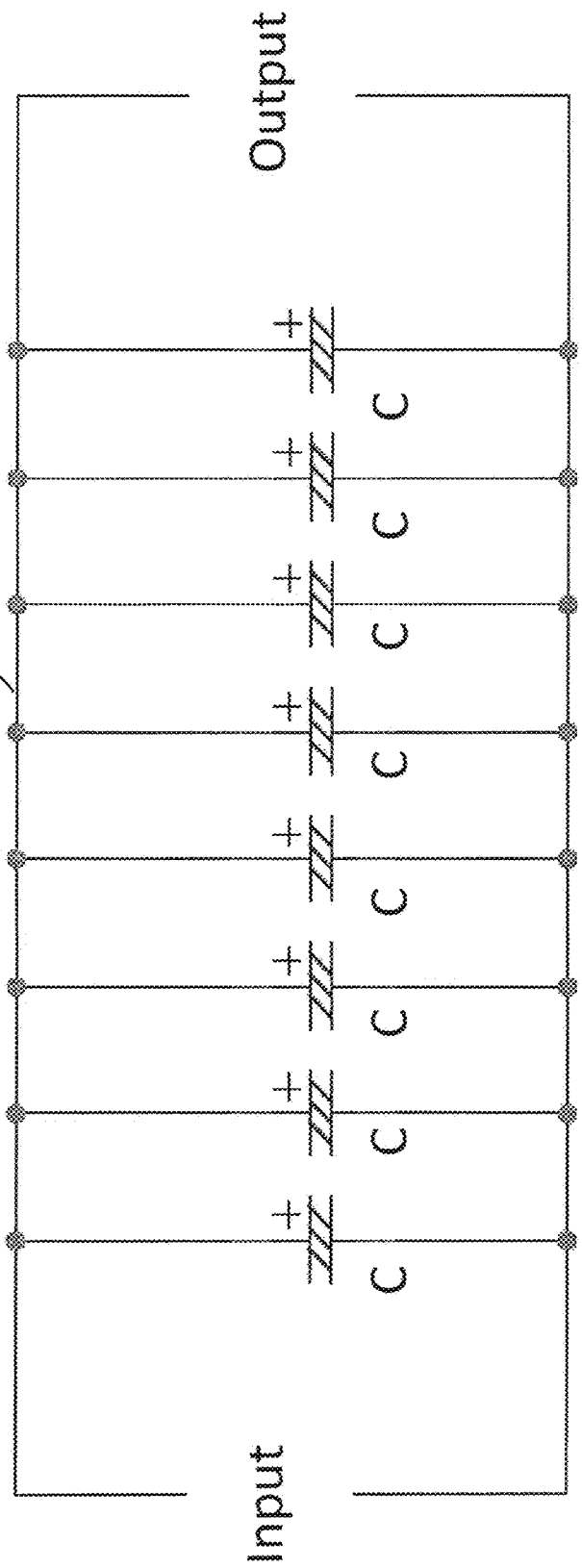
FIG. 5 is a circuit diagram showing an example of a capacitor circuit for a transfer pulse according to an embodiment of the present invention (C indicates a capacitor)
Figure 6:
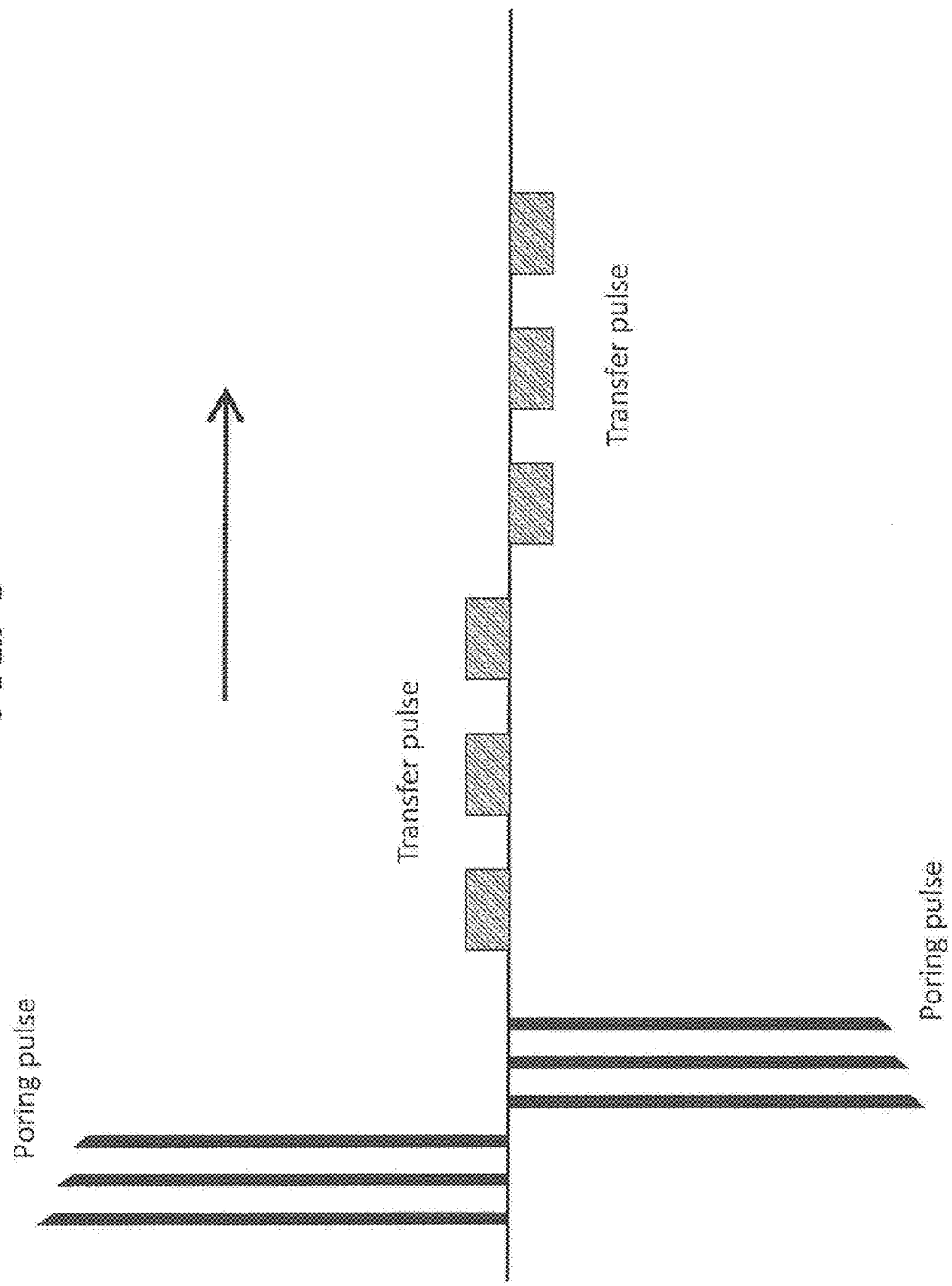
FIG. 6 is a schematic diagram showing an example of the waveform output of an electroporator according to an embodiment of the present invention (This figure shows an example of four-stage pulse output in which three poring pulses, three polarity-switched poring pulses, three transfer pulses, and three polarity-switched transfer pulses are output)

Therefore, the withstand voltage of the entire capacitor circuit 15 for a transfer pulse remains at 400 V, which is the same as the withstand voltage of the component capacitors, but eight capacitors are connected in parallel (see FIG. 5), and thus the capacitor capacity of the entire circuit is 2160 μF (270 μF×8).

Considering the capacitor capacity, pulses can be successively generated once to 20 times. It is also possible to generate no pulse (0 time).

(3) Polarity Switching of Output Voltage

The polarity switching circuit 8 can switch the voltage output by the capacitor circuit of the above-mentioned power source circuit for a poring pulse between output having a positive polarity (+) and output having a negative polarity (−). The polarity is switched by reversing plus/minus of the input.

Also, the polarity switching circuit 16 can switch the voltage output by the capacitor circuit of the power source circuit for a transfer pulse between output having a positive polarity (+) and output having a negative polarity (−).

(4) Poring Pulse/Transfer Pulse Switching

In the pulse generator of this embodiment, the poring pulse/transfer pulse switching control circuit 21 is connected to the merging point of the poring pulse generating power source circuit and the power source circuit for a transfer pulse.

In this pulse generator, the poring pulse/transfer pulse switching control circuit 21 controls whether to output a poring pulse or a transfer pulse.

(5) Pulse Control

In the pulse generator of this embodiment, the pulse control circuit 22 is connected to the output side of the poring pulse/transfer pulse switching control circuit 21 and performs overall control of the output pulse. With regard to the control in accordance with various input information, the power source control unit (not particularly shown) performs predetermined control.

(6) Apparatus Specification

An electroporator apparatus incorporating the pulse generator of this embodiment was manufactured. The outline of the specification of this electroporator apparatus is as shown in Table 3.

TABLE 3

|  | Poring pulse | | Transfer pulse |
|---|---|---|---|
|  | High-voltage mode | Low-voltage mode |  |
| Voltage | 801 to 3000 V | 100 to 800 V | 1 to 300 V |
| Pulse width | 0.1 to 15.0 ms | 0.1 to 50.0 ms | 0.1 to 99.9 ms |
| Pulse interval | 50 to 999.9 ms | 50 to 999.9 ms | 50 to 999.9 ms |
| Number of times | 0 to 9 times | 0 to 9 times | 0 to 20 times |
| Polarity switching | Positive/negative | Positive/negative | Positive/negative |
| Capacitor capacity | 55 µF | 995 µF | 2160 µF |

(7) Example of Output of Pulse Waveform

An oscilloscope was connected to this electroporator apparatus to detect an output waveform pattern. FIGS. 7 to 10 show the results (oscillograms) of the detected waveform patterns.

Output Waveform in High-Voltage Mode

Figure 7:
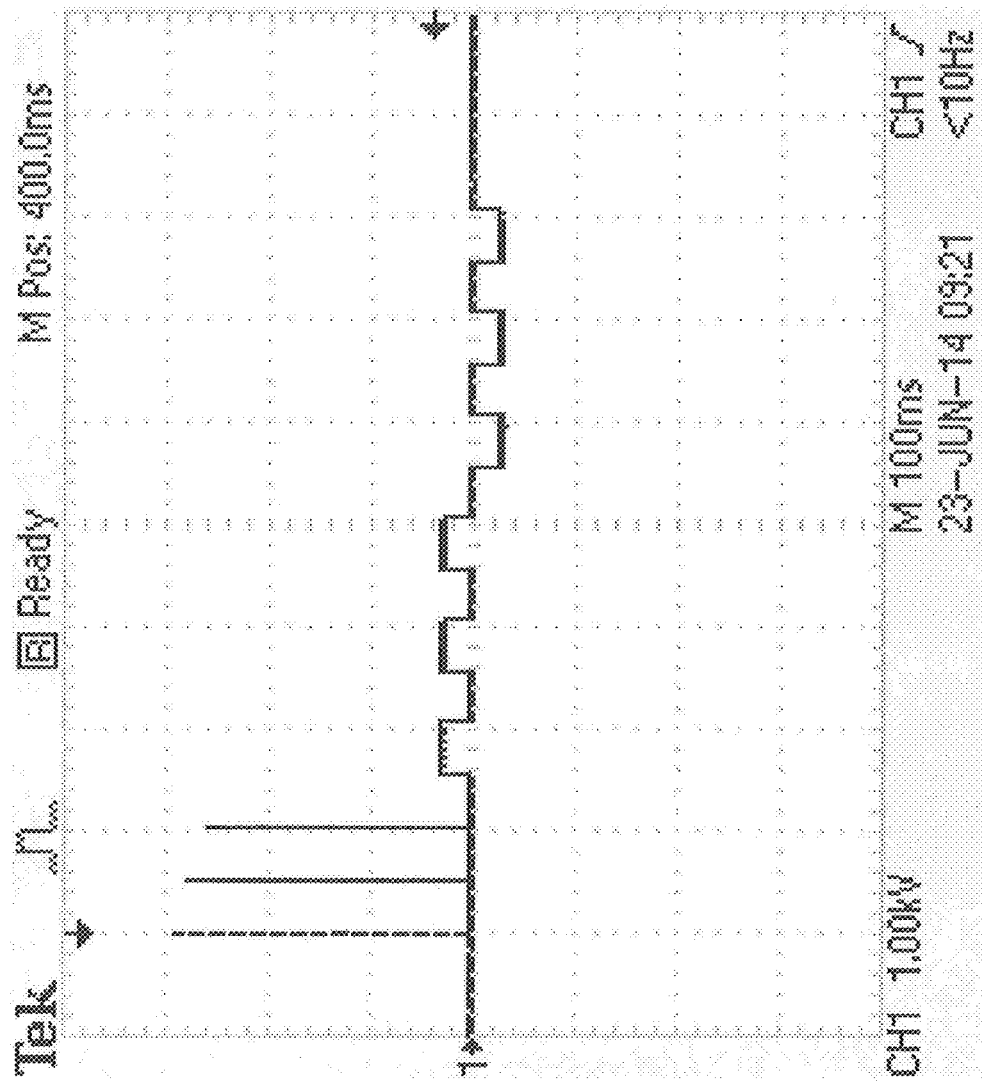
FIG. 7 is an oscillogram obtained by outputting a poring pulse in a high-voltage mode using an electroporator apparatus produced in Manufacturing Example 1 (This figure shows results of three-stage pulse output)
Figure 8:
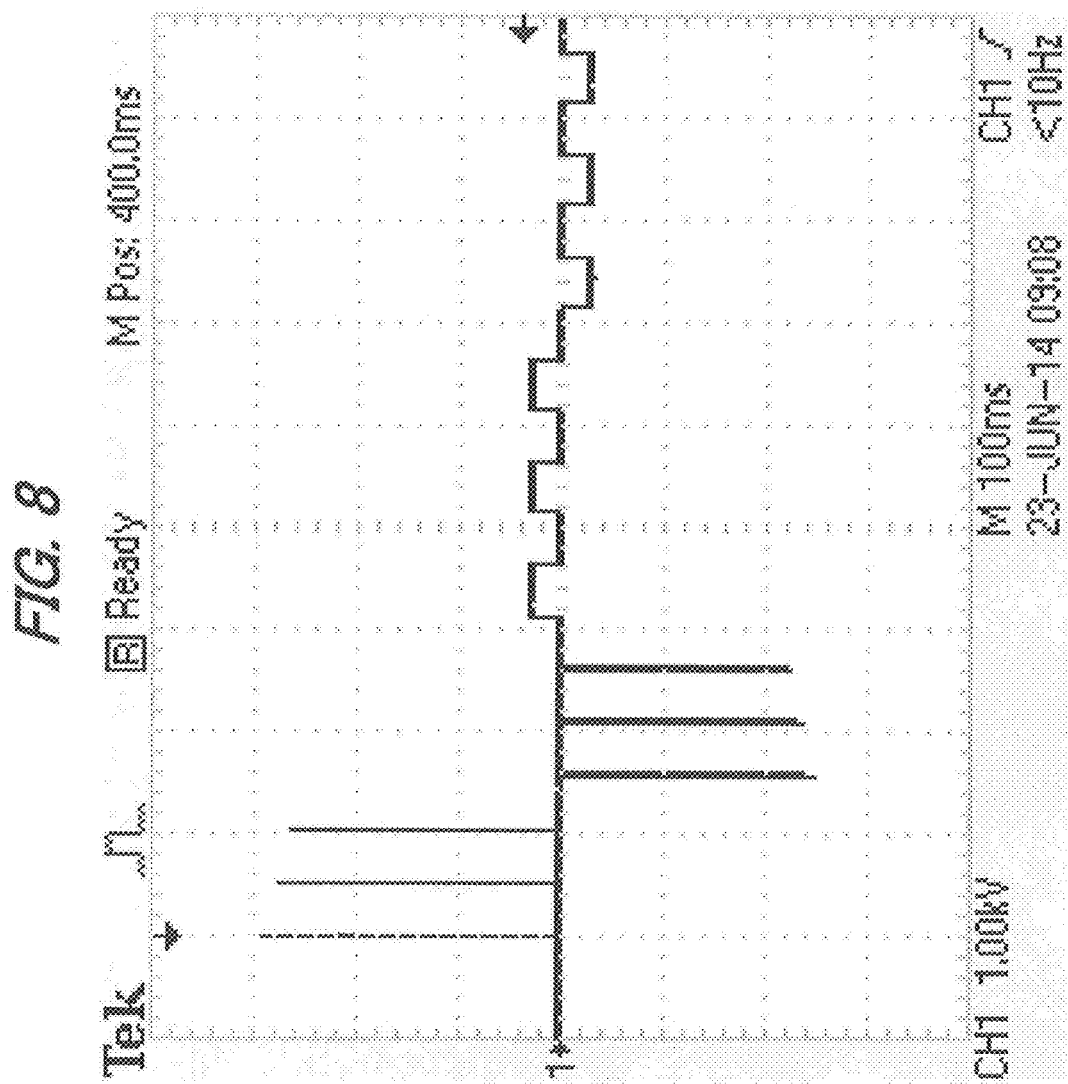
FIG. 8 is an oscillogram obtained by outputting a poring pulse in a high-voltage mode using the electroporator apparatus produced in Manufacturing Example 1 (This figure shows results of four-stage pulse output)

FIGS. 7 and 8 show examples of pulses output to subjects of 1 kΩ under predetermined set conditions (Pp: voltage of 3000 V, pulse width of 2.5 milliseconds, three times; Tp: voltage of 300 V, pulse width of 50 milliseconds, three times).

FIG. 7 shows an example of three-stage output in which three poring pulses, three transfer pulses, and three polarity-switched transfer pulses are output. The following are measurement results of the example shown in FIG. 7: the P-P value (peak to peak value) was 3240 V, the maximum voltage value was 2920 V, the minimum voltage value was −320 V, the Pp pulse width was 2.442 milliseconds, and Tp pulse width was 49.97 milliseconds.

FIG. 8 shows an example of four-stage output in which three poring pulses, three polarity-switched poring pulses, three transfer pulses, and three polarity-switched transfer pulses are output. The following are measurement results of the example shown in FIG. 8: the P-P value (peak to peak value) was 5400 V, the maximum voltage value was 2920 V, the minimum voltage value was −2480 V, the Pp pulse width was 3.160 milliseconds, and Tp pulse width was 49.64 milliseconds.

In both the examples shown in FIGS. 7 and 8, the actually measured maximum voltage value of a poring pulse was 2920 V. In this regard, regardless of the fact that a high-voltage pulse is output, the set voltage and the actual applied voltage value are extremely close to each other, thus showing that a stable high-voltage electric pulse can be output.

Output Waveform in Low-Voltage Mode

Figure 9:
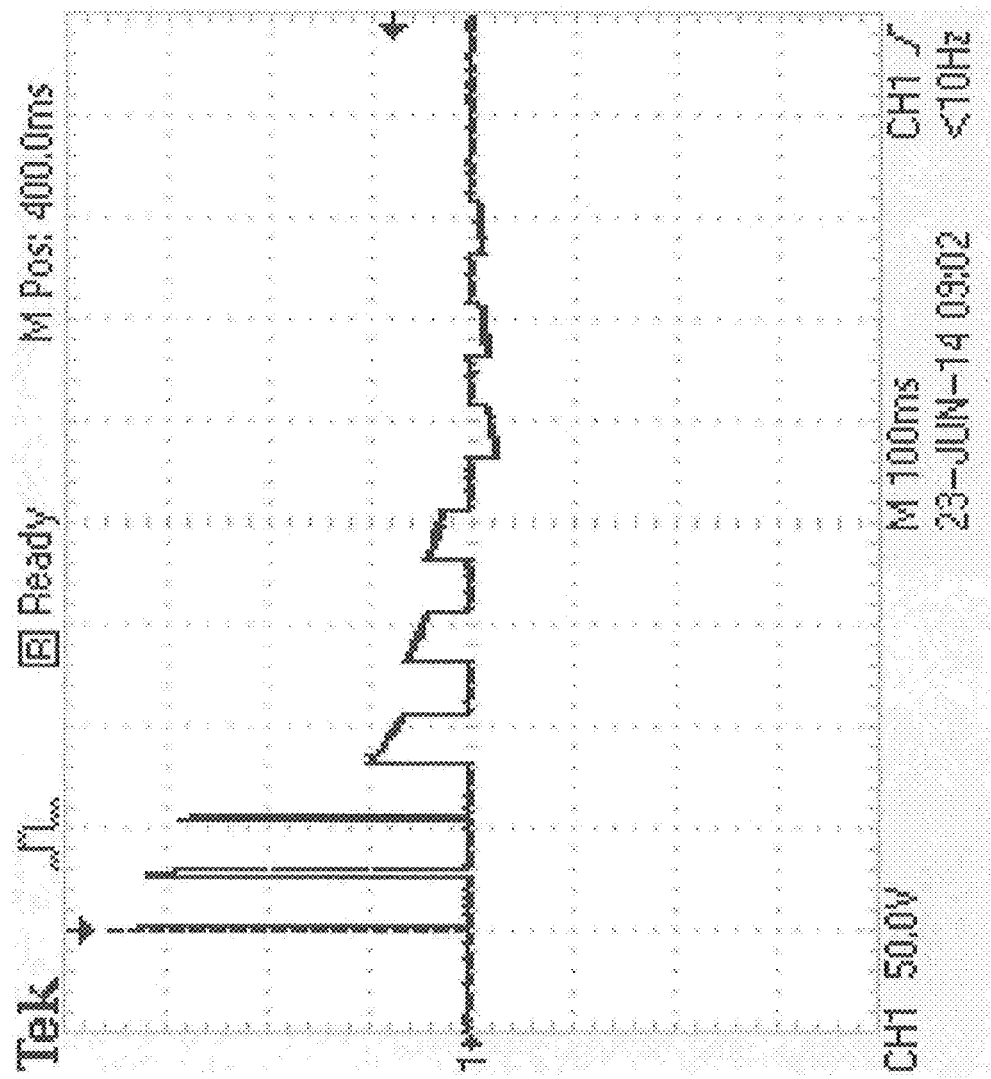
FIG. 9 is an oscillogram obtained by outputting a poring pulse in a low-voltage mode using the electroporator apparatus produced in Manufacturing Example 1 (This figure shows results of three-stage pulse output)
Figure 10:
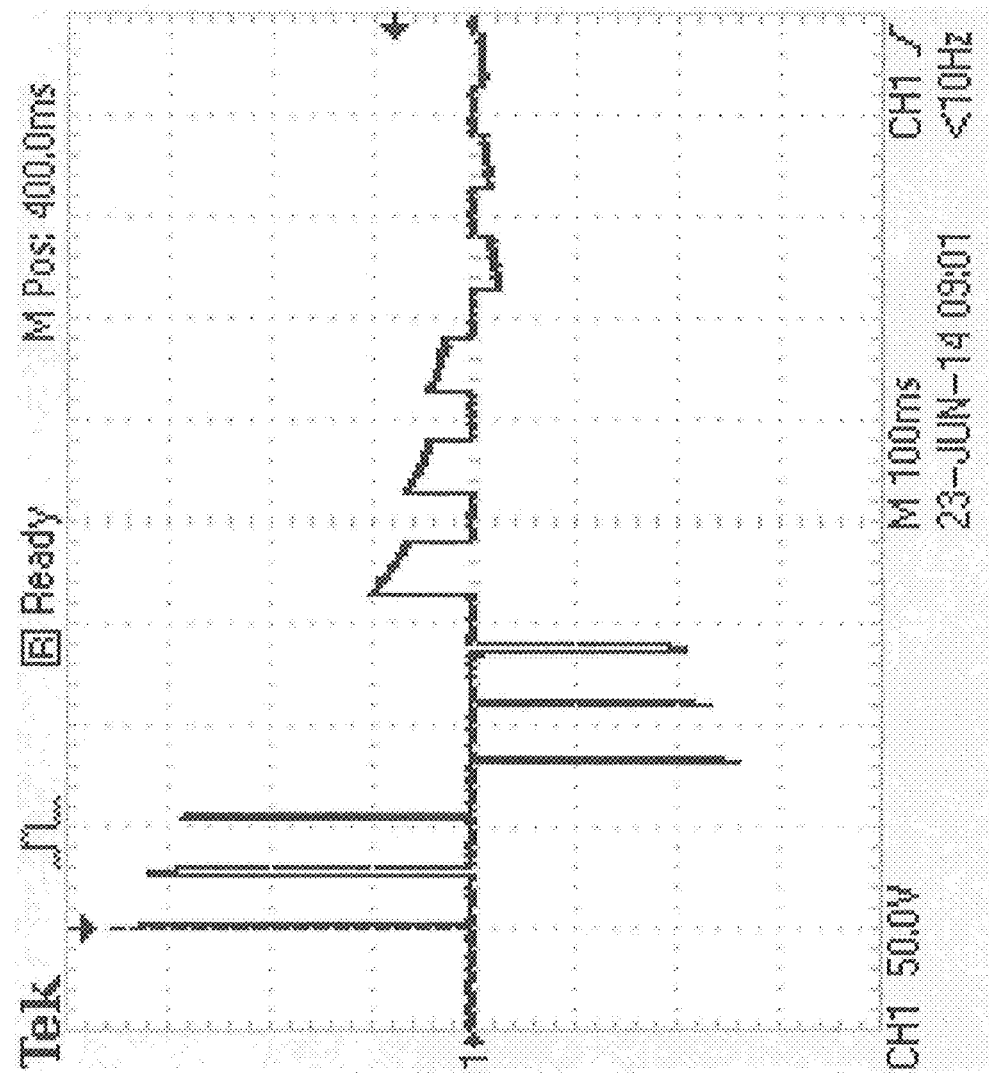
FIG. 10 is an oscillogram obtained by outputting a poring pulse in a low-voltage mode using the electroporator apparatus produced in Manufacturing Example 1 (This figure shows results of four-stage pulse output)

FIGS. 9 and 10 show examples of pulses output to subjects of 50Ω under predetermined set conditions (Pp: voltage of 180 V, pulse width of 5 milliseconds, three times; Tp: voltage of 50 V, pulse width of 50 milliseconds, three times).

FIG. 9 shows an example of three-stage output in which three poring pulses, three transfer pulses, and three polarity-switched transfer pulses are output. The following are measurement results of the example shown in FIG. 9: the P-P value (peak to peak value) was 192 V, the maximum voltage value was 180 V, the minimum voltage value was −12.0 V, the Pp pulse width was 5.211 milliseconds, and Tp pulse width was 50.01 milliseconds.

FIG. 10 shows an example of four-stage output in which three poring pulses, three polarity-switched poring pulses, three transfer pulses, and three polarity-switched transfer pulses are output. The following are measurement results of the example shown in FIG. 10: the P-P value (peak to peak value) was 310 V, the maximum voltage value was 180 V, and the minimum voltage value was −130 V.

In both the examples shown in FIGS. 9 and 10, the actually measured maximum voltage value of a poring pulse was 180 V.

Findings About Output Waveform

As shown in the oscillograms in FIGS. 7 to 10, it is shown that in this electroporator apparatus, multi-stage pulse generation in which a poring pulse and a transfer pulse are applied successively can be performed in both the high-voltage mode and the low-voltage mode.

In particular, it is shown that in the high-voltage mode for high-impedance subjects, a pulse having a regular shape similar to a square shape can be generated.

Example 1

Example of Gene Introduction into High-Impedance Subjects

The electroporator manufactured in Manufacturing Example 1 was used to perform a gene introduction test on a suspension of *E. coli* (Gram-negative bacterium) using multi-stage electroporation.

(1) Experimental Procedure

*E. coli* (DH5α) competent cells for EP were prepared. Cells in a logarithmic growth phase were collected, and then the competent cells were prepared according to a commonly used procedure.

The competent cells (10% glycerol solution containing $10^9$ to $10^{11}$ cells per sample) and a pUC19 vector (10 pg per sample) were mixed, and 20 µL of the resultant mixed solution was poured into a cuvette electrode with a 1-mm gap (manufactured by Nepa Gene Co., Ltd.). The series of operations was performed on ice in a cooled state.

The cuvette electrode into which the mixed solution of the cells and the DNA had been poured was inserted into a cuvette electrode chamber that was connected to the electroporator manufactured in Manufacturing Example 1, and three-stage electroporation treatment (one high-voltage poring pulse, five transfer pulses, and five polarity-switched transfer pulses) was performed under the conditions for an electric pulse shown in Table 4. The intervals between the pulses were set to 50 milliseconds.

On the other hand, as a comparative experiment, electroporation treatment (one high-voltage exponential pulse) was performed under the conditions for an electric pulse shown in Table 4 in the same manner, except that an electroporator apparatus (ECM 630, manufactured by BTX) for exponential output was used.

Then, the cells were plated on an LB agar medium containing ampicillin, and the number of colonies that were provided with drug resistance due to the introduction of pUC19 DNA and grew was counted. The number of colonies per microgram of the plasmid was calculated and evaluated as a gene introduction efficiency (cfu/μg). The gene introduction experiment was performed in duplicate, and an average value was calculated.

(2) Results

As a result, as shown in Table 5, it is shown that an extremely high gene introduction efficiency can be achieved by performing electric pulse treatment on the suspension (sample resistance value is about 7.7 kΩ) of *E. coli* that is the high-impedance subject using the multi-stage electroporator manufactured in Manufacturing Example 1.

Specifically, it is shown that when electric treatment is performed in which five transfer pulses and five polarity-switched transfer pulses are applied after a poring pulse of 2000 V is applied (Experiment 1-1), the gene introduction efficiency about 4.9 times higher than that in a case where high-voltage pulse treatment is performed at the same voltage using a conventional electroporator apparatus for exponential output (Experiment 1-3) can be achieved.

Also, it is shown that even when similar transfer pulses are applied after a poring pulse of 1800 V is applied using the multi-stage electroporator (Experiment 1-2), a gene introduction efficiency about 3.1 times higher than that in a case where a conventional electroporator apparatus is used (Experiment 1-3) can be achieved.

The reason why the voltage value of 2000 V was used in the comparative apparatus used in Experiment 1-3 is that this value was favorable when electroporation was performed in a preparatory experiment.

From these results, it is shown that multi-stage electroporation treatment can be performed on high-impedance subjects such as competent cells of *E. coli*, on which multi-stage electroporation treatment could not be conventionally performed, by using the electroporator manufactured in Manufacturing Example 1, and thus extremely efficient gene introduction can be achieved.

TABLE 4

| *E. coli* (DH5α) | | Apparatus according to the present invention (Experiment 1-1) | Apparatus according to the present invention (Experiment 1-2) | Comparative apparatus (Experiment 1-3) |
|---|---|---|---|---|
| Poring pulse (Pp) | Voltage (electric field intensity) | 2000 V (20 kV/cm) | 1800 V (18 kV/cm) | 2000 V (20 kV/cm) |
| | Pulse width | 2.5 ms | 2.5 ms | — |
| | Number of times | Once | Once | Once |
| | Polarity | Positive | Positive | Positive |

TABLE 4-continued

| *E. coli* (DH5α) | | Apparatus according to the present invention (Experiment 1-1) | Apparatus according to the present invention (Experiment 1-2) | Comparative apparatus (Experiment 1-3) |
|---|---|---|---|---|
| Transfer pulse 1 (Tp1) | Voltage | 150 V | 50 V | — |
| | Pulse width | 50 ms | 50 ms | — |
| | Number of times | Five times | Five times | — |
| | Polarity | Positive | Positive | — |
| Transfer pulse 2 (Tp2) | Voltage | 150 V | 50 V | — |
| | Pulse width | 50 ms | 50 ms | — |
| | Number of times | Five times | Five times | — |
| | Polarity | Negative | Negative | — |

TABLE 5

| *E. coli* (DH5α) | | Apparatus according to the present invention (Experiment 1-1) | Apparatus according to the present invention (Experiment 1-2) | Comparative apparatus (Experiment 1-3) |
|---|---|---|---|---|
| Gene introduction efficiency | $10^{10}$ cfu/μg | 1.400 ± 0.070 | 0.883 ± 0.113 | 0.285 ± 0.105 |
| | Relative value | 4.9 | 3.1 | 1.0 |

Example 2

Example of Gene Introduction into Low-Impedance Subjects

The electroporator manufactured in Manufacturing Example 1 was used to perform a gene introduction test on a suspension of animal cells using multi-stage electroporation.

(1) Experimental Procedure

HT1080 cells (human fibrosarcoma cells: adherent cells) were cultured, and then cells in an adhesion state were peeled by trypsin treatment. After confirming the peeling of the cells, the trypsin was removed, and then the cells were washed using an Opti-MEM medium (serum-free and antibiotic-free) and resuspended in the same liquid medium.

These HT1080 cells (Opti-MEM medium (serum-free and antibiotic-free) containing $10^6$ cells per sample) and a pCMV-EGFP vector (10 μg per sample) were mixed, and 100 μL of the mixed solution was poured into a cuvette electrode with a 2-mm gap (manufactured by Nepa Gene Co., Ltd.). The operations for handling these cells were performed at room temperature.

The cuvette electrode into which the mixed solution of the cells and the DNA had been poured was inserted into a cuvette electrode chamber that was connected to the electroporator manufactured in Manufacturing Example 1, and three-stage electroporation treatment (one or two high-voltage poring pulses, five transfer pulses, and five polarity-switched transfer pulses) was performed under the conditions for an electric pulse shown in Table 6. The intervals between the pulses were set to 50 milliseconds.

Moreover, a sample that was merely poured into a cuvette and on which the electroporation treatment was not performed was used as a control.

After that, the cells were cultured using a DMEM medium containing fetal bovine serum under regular culture conditions for 24 hours, and then the viability and the introduction rate were calculated in FACS analysis. The viability was represented by a ratio of the number of viable cells with respect to the total number of cells after 24-hour culture. case, a small amount of fluorescence relative to the total amount is emitted, and the results have no effect on the main issue of this embodiment.

TABLE 6

| HT1080 cells | | Experiment 2-1 | Experiment 2-2 | Experiment 2-3 | Experiment 2-4 | Experiment 2-5 | Experiment 2-6 | Control |
|---|---|---|---|---|---|---|---|---|
| Poring pulse (Pp) | Voltage V (electric field intensity V/cm) | 130 (650) | 140 (700) | 150 (750) | 160 (800) | 170 (850) | 180 (900) | — |
| | Pulse width ms | 2.5 | 2.5 | 2.5 | 2.5 | 2.5 | 2.5 | — |
| | Number of times | 2 | 2 | 2 | 2 | 2 | 2 | — |
| | Polarity | Positive | Positive | Positive | Positive | Positive | Positive | — |
| Transfer pulse 1 (Tp1) | Voltage V | 20 | 20 | 20 | 20 | 20 | 20 | — |
| | Pulse width ms | 50 | 50 | 50 | 50 | 50 | 50 | — |
| | Number of times | 5 | 5 | 5 | 5 | 5 | 5 | — |
| | Polarity | Positive | Positive | Positive | Positive | Positive | Positive | — |
| Transfer pulse 2 (Tp2) | Voltage V | 20 | 20 | 20 | 20 | 20 | 20 | — |
| | Pulse width ms | 50 | 50 | 50 | 50 | 50 | 50 | — |
| | Number of times | 5 | 5 | 5 | 5 | 5 | 5 | — |
| | Polarity | Negative | Negative | Negative | Negative | Negative | Negative | — |

TABLE 7

| HT1080 cells | | Experiment 2-1 | Experiment 2-2 | Experiment 2-3 | Experiment 2-4 | Experiment 2-5 | Experiment 2-6 | Control |
|---|---|---|---|---|---|---|---|---|
| Gene introduction rate | Viability | 85.1 | 84.5 | 81.2 | 82.9 | 76.2 | 73.4 | 91.9 |
| | Introduction rate | 70.1 | 71.6 | 75.4 | 76.7 | 81.9 | 82.5 | 0.4 |

Specifically, cells that had a normal form when analyzed in FACS analysis were used as the viable cells. The number of viable cells calculated in FACS analysis corresponded to the result of the number of viable cells calculated in Trypane blue staining and colony formation testing.

The gene introduction rate was determined by calculating the ratio of the number of cells in which the introduced EGFP gene was expressed with respect to the number of viable cells in FACS analysis.

(2) Results

As a result, as shown in Table 7, it is shown that gene introduction in which both the viability and introduction rate are favorable can be achieved by performing electric pulse treatment on the suspension (sample resistance value is about 41.6 kΩ) of animal cells that are the low-impedance subjects using the multi-stage electroporator that is manufactured in Manufacturing Example 1 and applies a poring pulse of 130 to 180 V.

From these results, it is shown that the electroporator manufactured in Manufacturing Example 1 is an apparatus that can perform highly efficient gene introduction using multi-stage electroporation even on a cell solution that is a low-impedance subject.

When an electric pulse treatment (e.g., one exponential pulse treatment at 100 to 200 V) is performed under regular conditions for an attenuated wave electric pulse method using an exponential type electroporator, such a high efficiency cannot be achieved.

In this experiment, fluorescence was detected in a very small number of cells of the control sample (0.4% of the viable cells). It is thought that the reason for this is that (i) HT1080 cells have strong autofluorescence, (ii) a DMEM medium emits a small amount of fluorescence having the same wavelength as that of GFP fluorescence, or (iii) some cells may phagocytose a plasmid, for example, but in any Findings from Examples 1 and 2

It is shown that genes can also be introduced into species and cells that are high-impedance subjects with an extremely high efficiency by using the multi-stage electroporator according to an embodiment of the present invention manufactured in Manufacturing Example 1.

Moreover, from the results as verified examples, it is shown that the multi-stage electroporation method is also actually effective for organisms that are the high-impedance subjects.

It is shown that the multi-stage electroporator according to an embodiment of the present invention manufactured in Manufacturing Example 1 is an apparatus that can perform favorable multi-stage electroporation on species and cells that are the low-impedance subjects.

From the results shown above, it is shown that the multi-stage electroporator according to an embodiment of the present invention is an apparatus that can achieve extremely favorable exogenous gene introduction into species and cells that are the low-impedance subjects and species and cells that are the high-impedance subjects.

INDUSTRIAL APPLICABILITY

With an embodiment of the present invention, an electroporator apparatus that can accommodate the increase in demand for electroporators and the diversification of applications and can be preferably used for a wide variety of species and cells can be provided in an efficiently manufacturable manner.

Accordingly, an embodiment of the present invention is expected to be extremely effectively used in all life-science research and development fields (e.g., molecular biology, genetics, microbiology, medicines, foods and beverages, agricultural chemistry, and zootechnical science) and in the medical therapy field.

Electroporators are apparatuses for achieving the easy and efficient introduction of nucleic acid molecules such as DNA, medicinal components, and the like into target cells by forming pores in the cell membranes of the target cells by electrical stimulation (electroporation method).

At life-science research and development sites, electroporators are recognized as an extremely important apparatus for introducing exogenous DNA, exogenous RNA, and the like into cells, and demand for electroporators has been increasing in many fields. Electroporators are extremely valuable apparatuses because they can be easily handled during operations and can be installed at relatively low cost, for example. This is also a big factor responsible for the increase in demand for electroporators.

However, increasing demand for electroporators in the industrial technology fields has resulted in demand for the introduction of electroporator apparatuses that can be used at sites in various fields. That is, as the subjects of electroporation become more diverse, the solutions that are suitable for the introduction targets (particularly the electric resistance of the solutions) and cytological properties (e.g., cell size and properties of the cell membrane) significantly vary depending on the species, tissues, and the like. Therefore, the introduction of an apparatus that can apply an electric pulse under conditions suitable for respective introduction targets has come into demand.

In particular, the difference in electric resistance (impedance) among the subjects has great influence on the electrical conditions of electroporation. When electric pulse treatment is performed on mammalian cells or the like, for example, a regular electroporation buffer and culture solution contain salts and buffer components, and thus the impedance of the subject to which an electric pulse is applied is relatively low. Therefore, when electroporation is performed on mammalian cells or the like, it is necessary to apply a relatively low-voltage electric pulse (relatively low-voltage electric pulse of about several tens of volts to several hundreds of volts that has an energy amount with which pores can be formed in cells).

On the other hand, when electric pulse treatment is performed on bacteria, yeasts, or the like, it is necessary to perform electroporation treatment in a high-impedance solution (solution having high electric resistance) to which glycerol, sugars, and the like have been added in order to suppress cell damage and maintain cell competency (transformation efficiency). Therefore, when electroporation is performed on bacteria or the like, it is necessary to apply a high-voltage electric pulse (high-voltage pulse of about several hundreds of volts to several thousands of volts).

In order to achieve electroporation by generating an electric pulse of several thousands of volts with respect to high-impedance subjects, a power source and a dedicated circuit for boosting input voltage and storing it in a capacitor to generate a high-voltage pulse are needed.

Normally, storing electric charge in a capacitor and generating a high-voltage electric pulse requires a dedicated direct-current power source and charging circuit (circuit that is necessary to charge a capacitor circuit: configuration including a series of circuits such as a switching circuit, a booster circuit, and a rectifier circuit) that are suitable for the desired voltage bands.

Here, a circuit in which capacitors are connected in series in order to generate a high voltage has a small electric capacity, and therefore, a problem arises in that sufficient electric capacity cannot be secured when electroporation is performed on a low-impedance subject, in which the voltage peak value of the output pulse attenuates greatly. That is, a problem arises in that when a voltage pulse is applied to a low-resistance subject, multiple pulses cannot be generated stably and sufficiently by merely employing a simple high voltage generating circuit.

Therefore, in the case where the generation of a low-voltage pulse and the generation of a high-voltage pulse are to be achieved in a single apparatus, it is necessary to provide a direct-current power source and a charging circuit for a low-voltage pulse of several tens of volts to several hundreds of volts in which electric capacity is sufficiently secured, and in addition to these, it is necessary to provide a direct-current power source and a charging circuit for a high voltage of several hundreds of volts to several thousands of volts. Thus, a problem of a significant increase in manufacturing cost arises.

Moreover, when cost is taken into consideration, chemical capacitors are generally used as high withstand voltage capacitors, but commercially available chemical capacitors have a withstand voltage of about 450 V and an electric capacity of about 560 μF at most. Therefore, it is currently difficult to procure chemical capacitors having a withstand voltage of higher than 500 V at low cost.

In particular, the problem of needing respective power source circuits for the high-voltage band and the low-voltage band becomes a major issue in the manufacturing of a multi-stage electroporator apparatus.

Here, a multi-stage electroporator is an apparatus for achieving multi-stage electric pulse generation that dramatically improves both the efficiency of introduction into introduction targets and the viability of the introduction targets.

Specifically, "multi-stage electroporator" refers to an apparatus that can perform electroporation in which a short-period high-voltage electric pulse (referred to as "poring pulse" or "Pp" hereinafter) and a low-voltage electric pulse having a long pulse width (referred to as "transfer pulse" or "Tp" hereinafter) are applied successively.

Such a multi-stage electroporator apparatus is manufactured and sold by manufacturers. An example thereof is NEPA21 Electroporator manufactured by Nepa Gene Co., Ltd. JP 2013-198637A is an example of a patent document that discloses a power source for an electroporator. (JP 2013-198637A refers to the poring pulse as a "poration pulse" and to the transfer pulse as a "driving pulse".)

However, a multi-stage electroporator apparatus has an apparatus configuration in which at least two types of power source circuits, namely a power source circuit for a poring pulse and a power source circuit for a transfer pulse, have already been installed therein.

Therefore, in the case where an apparatus that can generate pulses of voltages in a range of a low voltage of several tens of volts to a high voltage of several thousands of volts is to be realized as a multi-stage electroporator apparatus, it is necessary to further install a high-voltage power source circuit for a poring pulse of several hundreds of volts to several thousands of volts in addition to these two types of power source circuits (i.e., the power source circuit for a poring pulse of several tens of volts to several hundreds of volts, and the power source circuit for a transfer pulse).

In this regard, the further installation of a dedicated power source circuit (a direct-current power source and a charging circuit) becomes a big issue from the viewpoint of manufacturing cost. This is because the power source itself is expensive, and in addition, a separate circuit configuration including a series of capacitor charging circuits and a desired capacitor circuit is needed.

Furthermore, from the viewpoint of saving space in the apparatus housing (reducing the size of the apparatus product) as well, the addition of a separate power source circuit is a problem that should be avoided.

All existing multi-stage electroporator apparatuses can only generate a low-voltage poring pulse (several tens of volts to several hundreds of volts). That is, electroporator apparatuses that can perform electric pulse treatment that is optimum for multi-stage electroporation for high-impedance subjects (e.g., bacteria and yeasts) have not been realized yet.

It is an object of an embodiment of the present invention to provide, in an efficiently manufacturable manner, a multi-stage electroporator apparatus that solves the above-mentioned problems and can be preferably used for not only species and cells that are low-impedance subjects but also a wide variety of species and cells including bacteria, eukaryotic microorganisms, and the like that are high-impedance subjects.

Specifically, it is an object of an embodiment of the present invention to manufacture a multi-stage electroporator apparatus in an efficiently manufacturable manner, the electroporator apparatus being capable of adjusting the switching of the voltage of a poring pulse in an extremely broad range of several tens of volts to several thousands of volts depending on the difference in impedance among subjects and capable of stably and successively generating multiple poring pulses.

As a result of intensive research, the inventors of the present invention found that even when only one set of a direct-current power source and a capacitor charging circuit is used, a poring pulse generating power source circuit that can stably and successively output multiple poring pulses in an extremely broad range of several tens of volts to several thousands of volts can be realized by using, as the poring pulse generating power source circuit, a circuit including an n-stage Cockroft-Walton circuit and a branching-merging circuit connected to the output side of the Cockroft-Walton circuit. The branching-merging circuit includes a switching switch that is turned off in a high-voltage mode and turned on in a low-voltage mode and a circuit that is $m_1$-series $m_2$-parallel capacitors connected in series to the output side of the switching switch.

The present invention was arrived at based on the above-mentioned findings and specifically relates to aspects of the invention described below.

An electric pulse generator for an electroporator has a poring pulse generating means and a transfer pulse generating means. The electric pulse generator includes, as the poring pulse generating means:

(A) an n-stage Cockroft-Walton circuit (n represents any integer of 2 or more); and (B) a circuit that is branched from a branching point of wiring on an output side of the circuit recited in (A), and includes:

(b1) a switching switch that is turned off in a high-voltage mode and turned on in a low-voltage mode, a voltage value for switching between the high-voltage mode and the low-voltage mode being a voltage value in a range of 200 to 1400 V; and (b2) a circuit in which $m_2$ series of m 1 series-connected capacitors are connected in parallel (m 1 represents any integer of 1 or more, and $m_2$ represents any integer of 2 or more).

The switch recited in (b1) and the circuit recited in (b2) are connected in series, and wiring on an output side of the circuit recited in (b2) is merged with wiring on the output side of the circuit recited in (A) on the output side of the branching point.

In the electric pulse generator, the circuit (B) may include a diode on an output side of the circuit (b2) in the circuit (B), the diode being connected in a direction in which current flows toward the output side.

In the electric pulse generator, the capacitors of the circuit components included in the pulse generator may be capacitors having a withstand voltage of 500 V or lower.

In the pulse generator, the voltage value for switching between the high-voltage mode and the low-voltage mode may be a voltage value in a range of 500 to 1000 V.

In the pulse generator, circuitry constituting the poring pulse generating means may include only one set of a poring pulse generating direct-current power source and a capacitor charging circuit, a withstand voltage of the circuit (A) is any value in a range of 1500 to 5000 V in the high-voltage mode, and a total electric capacity of the circuit (A) and the circuit (b2) is any value in a range of 500 to 4000 μF in the low-voltage mode.

In the electric pulse generator, the integer n in the circuit (A) may be any integer in a range of 4 to 13, the integer m1 in the circuit (b2) may be any integer in a range of 2 to 6, and the integer m2 in the circuit (b2) may be any integer in a range of 2 to 10.

In the electric pulse generator, the pulse generator may include a means for controlling switching of a polarity of output voltage.

In the electric pulse generator, the pulse generator may include a means for pulse control of an output pulse.

An electroporator apparatus provided with the electric pulse generator.

A method for introducing an exogenous gene using electroporation may use the electroporator apparatus.

With an embodiment of the present invention, it is possible to manufacture a multi-stage electroporator apparatus in an efficiently manufacturable manner, the electroporator apparatus being capable of adjusting the switching of the voltage of a poring pulse in an extremely broad range of several tens of volts to several thousands of volts depending on the difference in impedance among subjects and capable of stably and successively generating multiple poring pulses.

Accordingly, an embodiment of the present invention can provide, in an efficiently manufacturable manner, a multi-stage electroporator apparatus that can be preferably used for not only species and cells that are low-impedance subjects but also a wide variety of species and cells including bacteria, eukaryotic microorganisms, and the like that are high-impedance subjects.

Moreover, it is possible to manufacture a high-performance multi-stage electroporator apparatus regardless of the fact that the poring pulse generating power source circuit according to an embodiment of the present invention has a simple circuit configuration. A reduction in size due to space saving is also expected.

Furthermore, use of the apparatus according to an embodiment of the present invention makes it possible to introduce exogenous genes into species and cells that are low-impedance subjects as well as species and cells that are high-impedance subjects with an extremely favorable gene introduction efficiency.

Obviously, numerous modifications and variations of the present invention are possible in light of the above teachings. It is therefore to be understood that within the scope of the appended claims, the invention may be practiced otherwise than as specifically described herein.

The invention claimed is:

1. An electric pulse generator for an electroporator, comprising:
   a poring pulse generator; and
   a transfer pulse generator,
   wherein the poring pulse generator comprises an n-stage Cockroft-Walton circuit, where n represents an integer of 2 or more, and a first circuit that is branched from a branching point of wiring on an output side of the n-stage Cockroft-Walton circuit, the first circuit includes a switching switch that is turned off in a high-voltage mode and turned on in a low-voltage mode, a voltage value for switching between the high-voltage mode and the low-voltage mode being in a range of 200 to 1400 V, the first circuit includes a second circuit in which $m_2$ series of $m_1$ series-connected capacitors are connected in parallel, where $m_1$ represents an integer of 1 or more, and $m_2$ represents an integer of 2 or more, the switching switch and the second circuit are connected in series, and first wiring, which is disposed on an output side of the second circuit, is merged with second wiring, which is disposed on the output side of the n-stage Cockroft-Walton circuit, on the output side of the branching point, and a withstand voltage of the n-stage Cockroft-Walton circuit is a value in a range of 1500 to 5000 V in the high-voltage mode.

2. The electric pulse generator according to claim 1, wherein the first circuit includes a diode on an output side of the second circuit in the first circuit, the diode being connected in a direction in which current flows toward the output side.

3. The electric pulse generator according to claim 1, wherein the capacitors of the second circuit have a withstand voltage of 500 V or lower.

4. The electric pulse generator according to claim 1, wherein the voltage value for switching between the high-voltage mode and the low-voltage mode is a voltage value in a range of 500 to 1000 V.

5. The electric pulse generator according to claim 1, wherein the poring pulse generator includes only one set of a poring pulse generating direct-current power source and a capacitor charging circuit, and a total electric capacity of the n-stage Cockroft-Walton circuit and the second circuit is any value in a range of 500 to 4000 µF in the low-voltage mode.

6. The electric pulse generator according to claim 1, wherein the integer n in the n-stage Cockroft-Walton circuit is any integer in a range of 4 to 13, the integer $m_1$ in the second circuit is any integer in a range of 2 to 6, and the integer $m_2$ in the second circuit is any integer in a range of 2 to 10.

7. The electric pulse generator according to claim 1, further comprising:
   at least one polarity switching circuit configured to control switching of a polarity of output voltage.

8. The electric pulse generator according to claim 1, further comprising:
   at least one pulse control circuit configured to control an output pulse.

9. An electroporator apparatus including the electric pulse generator according to claim 1.

10. The electric pulse generator according to claim 2, wherein the capacitors of the second circuit have a withstand voltage of 500 V or lower.

11. The electric pulse generator according to claim 2, wherein the voltage value for switching between the high-voltage mode and the low-voltage mode is a voltage value in a range of 500 to 1000 V.

12. The electric pulse generator according to claim 2, wherein the poring pulse generator includes only one set of a poring pulse generating direct-current power source and a capacitor charging circuit, and a total electric capacity of the n-stage Cockroft-Walton circuit and the second circuit is any value in a range of 500 to 4000 µF in the low-voltage mode.

13. The electric pulse generator according to claim 2, wherein the integer n in the n-stage Cockroft-Walton circuit is any integer in a range of 4 to 13, the integer $m_1$ in the second circuit is any integer in a range of 2 to 6, and the integer $m_2$ in the second circuit is any integer in a range of 2 to 10.

14. The electric pulse generator according to claim 2, further comprising:
   at least one polarity switching circuit configured to control switching of a polarity of output voltage.

15. The electric pulse generator according to claim 2, further comprising:
   at least one pulse control circuit configured to control an output pulse.

16. An electroporator apparatus including the electric pulse generator according to claim 2.

17. The electric pulse generator according to claim 3, wherein the voltage value for switching between the high-voltage mode and the low-voltage mode is a voltage value in a range of 500 to 1000 V.

18. The electric pulse generator according to claim 3, wherein the poring pulse generator includes only one set of a poring pulse generating direct-current power source and a capacitor charging circuit, and a total electric capacity of the n-stage Cockroft-Walton circuit and the second circuit is any value in a range of 500 to 4000 µF in the low-voltage mode.

19. The electric pulse generator according to claim 3, wherein the integer n in the n-stage Cockroft-Walton circuit is any integer in a range of 4 to 13, the integer $m_1$ in the second circuit is any integer in a range of 2 to 6, and the integer $m_2$ in the second circuit is any integer in a range of 2 to 10.

20. A poring pulse generator, comprising:
   an n-stage Cockroft-Walton circuit, where n represents an integer of 2 or more; and
   a first circuit that is branched from a branching point of wiring on an output side of the n-stage Cockroft-Walton circuit,
   wherein the first circuit includes a switching switch that is turned off in a high-voltage mode and turned on in a low-voltage mode, a voltage value for switching between the high-voltage mode and the low-voltage mode being in a range of 200 to 1400 V, the first circuit includes a second circuit in which $m_2$ series of $m_1$ series-connected capacitors are connected in parallel, where $m_1$ represents an integer of 1 or more, and $m_2$ represents an integer of 2 or more, the switching switch and the second circuit are connected in series, and first wiring, which is disposed on an output side of the second circuit, is merged with second wiring, which is disposed on the output side of the n-stage Cockroft-Walton circuit, on the output side of the branching point, and a withstand voltage of the n-stage Cockroft-Walton circuit is a value in a range of 1500 to 5000 V in the high-voltage mode.

* * * * *